(12) United States Patent
Miller et al.

(10) Patent No.: US 8,735,638 B2
(45) Date of Patent: May 27, 2014

(54) TRANSFORMATION OF BIOMASS

(75) Inventors: Ian James Miller, Wellington (NZ);
Rhys Antony Batchelor, Palmerston (NZ)

(73) Assignee: Aquaflow Bionomic Corporation Limited, Nelson (NZ)

( * ) Notice: Subject to any disclaimer, the term of this patent is extended or adjusted under 35 U.S.C. 154(b) by 93 days.

(21) Appl. No.: 13/063,398

(22) PCT Filed: Sep. 11, 2009

(86) PCT No.: PCT/NZ2009/000192
§ 371 (c)(1),
(2), (4) Date: Jun. 14, 2011

(87) PCT Pub. No.: WO2010/030196
PCT Pub. Date: Mar. 18, 2010

(65) Prior Publication Data
US 2011/0245444 A1    Oct. 6, 2011

Related U.S. Application Data

(60) Provisional application No. 61/096,277, filed on Sep. 11, 2008.

(51) Int. Cl.
*C07C 4/00* (2006.01)
*C07C 2/00* (2006.01)
*C07C 1/00* (2006.01)

(52) U.S. Cl.
USPC ............ 585/240; 585/469; 585/638; 585/733

(58) Field of Classification Search
USPC .................................. 585/240, 469, 638, 733
See application file for complete search history.

(56) References Cited

U.S. PATENT DOCUMENTS

| | | | |
|---|---|---|---|
| 4,341,038 A | 7/1982 | Bloch et al. | |
| 5,476,787 A | 12/1995 | Yokoyama et al. | |
| 6,057,262 A | 5/2000 | Derbyshire et al. | |
| 6,180,845 B1 | 1/2001 | Catallo et al. | |
| 6,338,866 B1 | 1/2002 | Criggall et al. | |
| 6,350,350 B1 | 2/2002 | Jensen et al. | |
| 2005/0112735 A1 | 5/2005 | Zappi et al. | |
| 2006/0004237 A1 | 1/2006 | Appel et al. | |
| 2006/0060526 A1* | 3/2006 | Binning et al. | 210/603 |
| 2007/0161095 A1 | 7/2007 | Gurin | |
| 2008/0216391 A1 | 9/2008 | Cortright et al. | |
| 2009/0071064 A1 | 3/2009 | Machacek et al. | |

FOREIGN PATENT DOCUMENTS

| | | |
|---|---|---|
| CA | 2624510 A1 | 4/2007 |
| WO | 2008/034109 A1 | 3/2008 |
| WO | 2008/103204 A2 | 8/2008 |
| WO | 2008/134836 A2 | 11/2008 |
| WO | 2008/151149 A2 | 12/2008 |
| WO | 2009/064204 A2 | 5/2009 |

OTHER PUBLICATIONS

Kruse, A., et al., "Biomass Conversion in Water at 330-410 ° C. and 30-50 MPa. Identification of Key Compounds for Indicating Different Chemical Reaction Pathways", Ind. Eng. Chem. Res., 2003, pp. 267-279, vol. 42.
Robinson, J. Michael, et al., "The use of catalytic hydrogenation to intercept carbohydrates in a dilute acid hydrolysis of biomass to effect a clean separation from lignin", Biomass and Bioenergy, 2004, pp. 473-483, vol. 26.
Sharma, D. K., "Two-Step Process for the Selective Production of Fermentable Sugars and Ethanol from Biomass Residues (Agricultural Wastes)", Cellulose Chemistry and Technology, 1989, pp. 45-51, vol. 23.
Williams, Paul T., "Composition of Products from the Supercritical Water Gasification of Glucose: A Model Biomass Compound", Ind. Eng. Chem. Res., 2005, pp. 8739-8749, vol. 44.
International Search Report for International Application No. PCT/NZ2009/000192 dated Dec. 9, 2009.
Miller and Fellows "Catalytic effects during cellulose liquefaction" Fuel (1985) 64: 1246-1250.
Miller and Saunders "Reactions of possible cellulose liquefaction intermediates under high pressure liquefaction conditions", Fuel (1987) 66: 123-129.
Ferrier et al. "The products of zinc chloride promoted decomposition of cellulose in aqueous phenol at 350° C." Carbohyd. Res (1992) 237:79-86.
Ferrier et al "Isotype studies of the transfer of carbon atoms of carbohydrate derivatives into aromatic compounds (especially xanthene) under degradation conditions," Carbohyd. Res (1992) 237:87-94.
International Search Report for International Application No. PCT/NZ2009/000193 dated Jan. 12, 2010.
Dote et al., "Recovery of liquid fuel from hydrocarbon-rich microalgae by thermochemical liquefaction," Fuel, 1994, pp. 1855-1857, vol. 73, No. 12.
Yang et al., "Analysis of energy conversion characteristics in liquefaction of algae", Resources, Conservation and Recycling, 2004, pp. 21-33, vol. 43, No. 1.

* cited by examiner

*Primary Examiner* — Samantha Shterengarts
(74) *Attorney, Agent, or Firm* — Sughrue Mion, PLLC (57) ABSTRACT

A method for processing biomass comprising heating an aqueous slurry comprising biomass, water and a phosphate catalyst in a pressure vessel at a temperature of about 150° C. to about 500° C. to produce a mixture comprising a dispersion of an organic phase and an aqueous phase.

17 Claims, 1 Drawing Sheet

TRANSFORMATION OF BIOMASS

CROSS REFERENCE TO RELATED APPLICATION

This application is a National Stage of International Application No. PCT/NZ2009/000192 filed Sep. 11, 2009, which claims priority from U.S. Provisional Patent Application No. 61/096,277 filed Sep. 11, 2008, the contents of all of which are incorporated herein by reference in their entirety.

FIELD OF THE INVENTION

The present invention relates to a process for producing one or more organic chemical products or fuel from biomass, and in particular from microalgae, by means of high pressure hydrothermal treatment in the presence of phosphate catalysts.

BACKGROUND TO THE INVENTION

A major problem for future economies will be to find alternatives sources of fuel and chemical precursors as the natural oil supplies run down, or are at least unable to fully supply demand at low cost. One such potential source of replacements is biomass.

A biofuel may be considered as any fuel, or component(s) which can contribute to a fuel, which is derived from biomass.

Biofuels are intended to provide an alternative to fossil fuels, and may be used as a source of energy, such as in transport fuels or for generating electricity, or for providing heat. Biomass can also be used to make other useful organic chemical products, and eventually it will be highly desirable to be able to make many chemical intermediates, solvents and polymer intermediates from biomass.

Various means of converting biomass to fuels or to useful organic chemical products have been proposed, such as fermentation, gasification and pyrolysis, however such technologies are limited because of a combination of the cost of implementation, limited product range, scale dependence and extensive waste products. Apart from fermentation, many such technologies work best when the initial biomass is dry, and many sources of biomass, particularly algae, are most readily obtained in a highly wet form.

Methods of converting wet biomass to organic chemical products are known. One such technology is high-pressure liquefaction, which occurs in two variants. One is to hydrogenate the biomass directly by heating a slurry of biomass under a pressurized atmosphere of hydrogen in the presence of a catalyst. The alternative is simply to liquefy the biomass by heating a slurry of biomass under pressure, effectively trying to accelerate the process that led to the formation of natural oil reserves. The advantage of the second process is that biomass can be converted to a liquid that is more easily transported to a refinery, where the advantages of scale can be applied, both to the fuel processing, and to the hydrogen production. Direct hydrogenation is only feasible for the smaller scale production from biomass if the product does not need further refining, and that is not usually the case.

The concept of heating biomass in water to transform it to fuel and other organic chemical products has been reported. Thus Catallo and Junk (U.S. Pat. No. 6,180,845) have shown that heating cellulose in water under near-critical to super-critical conditions led to the production of phenol and substituted phenols, substituted benzene derivatives, cyclopentanone and methylated naphthalenes. Reaction of lignin under the same conditions produced various substituted phenols, naphthalenes and indenes and lipids. Highly nitrogenated biomass gave products particularly rich in phenol, toluene, phenylethanone, substituted pyridines and indole.

Previously, it has been reported (I. J. Miller and S. K. Fellows, Catalytic effects during cellulose liquefaction, *Fuel*, 1985, 64: 1246-1250; and I. J. Miller and E. R. Saunders, Reactions of possible cellulose liquefaction intermediate under high-pressure liquefaction conditions, *Fuel*, 1987, 66: 123-129) that the heating of cellulosic biomass to 350-375° C. in the presence of phenol and other catalysts produces phenol, and similar compounds as noted above, e.g. cresols, polyhydroxybenzenes, tetralins and indanes. The difference between these processes and the processes described in U.S. Pat. No. 6,180,845 is that in the former processes significant additional hydrogenation occurred without the use of hydrogen. The liquefaction catalysts so used tended to be acidic in nature, the most basic being sodium dihydrogen phosphate, which gives solutions of pH in the vicinity of 6.3. Reasons for the difference in products presumably include the catalytic involvement of phenol in depolymerising the cellulose, thus holding the carbohydrate in the form of phenol glycosides, as well as the general acidity of the process. (See R. J. Ferrier, W. B. Severn, R. H. Furneaux and I. J. Miller, "The products of zinc chloride promoted decomposition of cellulose in aqueous phenol at 350°", *Carbohydr. Res.* 1992, 237: 79-86; and R. J. Ferrier, W. B. Severn, R. H. Furneaux and I. J. Miller, "Isotope studies of the transfer of carbon atoms of carbohydrate derivatives into aromatic compounds", *Carbohydr. Res.* 1992, 237: 87-94).

Therefore, from previous work it is known that the type of products obtained by liquefying biomass under hydrothermal conditions may be able to be altered by alteration of the conditions and the media in which the liquefaction takes place While land-based biomass is of obvious interest as a feed material for hydrothermal processing, of particular interest are microalgae. Microalgae are possibly the fastest growing plants on the planet, and therefore offer the greatest yield per unit area, which may be of considerable importance to overcome the problem of getting sufficient raw material from a smaller area to get the economies of scale required for chemical processing.

Microalgae are unusual amongst plants in that they tend to store energy in lipids as opposed to the more usual carbohydrates, and it is possible, by growing microalgae under controlled conditions, to raise the lipid levels of some microalgae to in excess of 50% by weight (wt. %). However, the use of photo-bioreactors needed to achieve such lipid yields greatly increase the overall capital and operating costs.

Microalgae can be harvested from adventitious sources, such as water treatment systems, however such microalgae generally devote most of their photochemically derived energy to reproduction, which means that the lipid fraction may be relatively low, and the biomass may largely comprise nitrogen-rich materials such as protein and nucleic acids. As noted above, Catallo and Junk report that hydrothermal treatment of nitrogen-rich biomass gave similar products as other biomass, although indole and pyridine were also formed, the latter being a highly valuable solvent.

It is clear that using adventitious microalgae that must be produced anyway, e.g. in sewage treatment ponds, saves considerable expense in not having to grow specific microalgae in special systems or ponds, however such algae do not have the high lipid content of specially grown microalgae. To date, there are very few clearly successful processes that produce and sell economically and in good volume fuels and chemicals from biomass, and seemingly none from adventitious microalgae. Accordingly, a process that would make desirable fuel from such algae with low lipid content would be important.

It is also desirable to find a process that, by using different conditions but conditions not so different that different processing equipment is required, can be used to make different products so as to take advantage of different market changes. The ability to change the direction of chemical reactions requires agents that alter the relative rates of different reaction pathways, which requires catalysts that can carry out different functions.

It is therefore an object of the present invention to provide a method for processing biomass into organic chemical products that may go at least some way towards addressing at least one of the foregoing problems or which will at least provide the public with a useful choice.

SUMMARY OF THE INVENTION

In a first aspect, the present invention relates to a method for processing biomass comprising heating an aqueous slurry comprising biomass, water and a phosphate catalyst in a pressure vessel at a temperature of about 150° C. to about 500° C. to produce a mixture comprising a dispersion of an organic phase and an aqueous phase.

In one embodiment the present invention relates to a method for producing one or more organic chemical products from biomass comprising:
(i) heating an aqueous slurry comprising biomass and water in a pressure vessel at a temperature of about 150° C. to about 500° C. in the presence of a phosphate catalyst to produce a mixture comprising a dispersion of an organic phase and an aqueous phase, and
(ii) optionally separating one or more organic chemical products from the mixture.

In one embodiment the aqueous slurry comprises about 1 to about 80% by weight biomass.

In one embodiment the aqueous slurry comprises 1 to about 30% by weight phosphate catalyst.

In one embodiment the biomass is heated at an autogenous pressure. In various embodiments the biomass is heated at a pressure of about 1 to about 35 MPa.

In one embodiment the biomass is heated for about 1 to about 240 or about 5 to about 240 minutes or more.

In one embodiment the biomass is heated for a first period at a first temperature for about 1 to about 120 minutes or more and for a second period at a second temperature for about 1 to 120 minutes or more. In various embodiments the first temperature is about 150 to about 373° C. and the second temperature is about 374 to about 500° C.

In one embodiment phosphate catalyst comprises a phosphate ion and a counter ion. The counterion may be varied, or the concentration of the catalyst may be varied, in order to alter the product distribution, as described below.

In various embodiments the phosphate catalyst comprises a phosphate anion and one or more monovalent counterions. The counterion is preferably selected from the group comprising hydrogen, lithium, sodium, potassium, rubidium, caesium and ammonium ions, or any two or more thereof.

In other embodiments the phosphate catalyst comprises a phosphate anion and one or more divalent counterions. The divalent counterion is preferably selected from the group comprising magnesium, calcium, barium, strontium, zinc, cadmium, copper, nickel, cobalt, manganese, vanadyl, tin, lead and ferrous ions, or any two or more thereof.

In yet other embodiments the phosphate catalyst comprises a phosphate anion and one or more trivalent counterions. The trivalent counterion is preferably selected from the group comprising ferric, aluminium, chromic, scandium and rare earths ions, or any two or more thereof. In one embodiment where the phosphate catalyst comprises a phosphate anion and one or more trivalent counterions the temperature is held between 300-374° C. and the reaction time is between 5 minutes and 35 minutes.

In an alternative embodiment the phosphate catalyst comprises a phosphate anion and one or more monovalent counterions, or one or more divalent counterions, or one or more trivalent counterions, or any combination of any two or more thereof. The counterion is preferably selected from the group comprising hydrogen, lithium, sodium, potassium, rubidium, caesium, ammonium, magnesium, calcium, barium, strontium, zinc, cadmium, copper, nickel, cobalt, manganese, vanadyl, tin, lead, ferrous, ferric, aluminium, chromic, scandium and rare earths ions, or any two or more thereof.

In various embodiments the pH of the aqueous slurry is adjusted to a pH of about 7 to about 11, such as by the addition of ammonia (particularly to increase the production of nitrogen heterocycles).

In other embodiments the pH of the aqueous slurry is adjusted to a pH of about 3 to about 7, such as by the addition of any acid, including phosphoric acid, which may also be the phosphate catalyst. In yet other embodiments the pH of the aqueous slurry is adjusted to a pH of about 5 to about 7, preferably to maximise the use of the dihydrogen phosphate anion. In still other embodiments the pH of the aqueous slurry is adjusted to a pH of about 7 to about 8.5, preferably to maximise the use of the monohydrogen phosphate anion.

In alternative embodiments the pH of the aqueous slurry is adjusted to a pH of about 8.5 to about 11, preferably to maximise the use of the phosphate anion.

In various embodiments the biomass is selected from the set comprising algal biomass, cellulosic biomass, proteinaceous biomass and seaweed, or any combination of any two or more thereof. In embodiments where the biomass is algae, such as microalgae, preferably the aqueous slurry comprises about 2% to about 80% dry weight equivalent of algae, about 10% to about 30% dry weight equivalent of algae, or about 5% to about 40% dry weight equivalent of algae In one embodiment the phases are separated, and the aqueous phase may optionally be extracted with an organic solvent immiscible in water to recover water-soluble organic material.

In a further embodiment, the mixture is subjected to a solvent extraction step to separate the organic phase from the aqueous phase.

In a further embodiment, any organic phase may then undergo further extraction stages to separate classes of products, including the removal of inorganic contaminants, until solvent and components are recovered by distillation.

In a further embodiment, the aqueous phase from the extracted mixture may have its pH altered and the solution may be further extracted to obtain further products.

In a further embodiment, the mixture may be distilled first.

In a further embodiment, such a distillation may be achieved by flashing off the water from the pressurized vessel through a controlled release of pressure.

In one embodiment the mixture is subjected to a sequence of solvent/aqueous extraction steps with sequential changes of pH to separate organic chemical products from the mixture.

In one embodiment the one or more organic chemical products include but are not limited to pyrazines such as methyl, dimethyl, ethyl or ethylmethyl pyrazine and trimethyl pyrazine; hydrocarbons such as toluene, xylene, ethyl benzene, styrene, alkanes and alkenes including but not limited to 1-nonene, pentadecene, and heptadecene, alkanes including but not limited to pentadecane, and heptadecane; methylated pyrroles, imides such as N-methyl and N-ethyl succinimide; amides such as hexadecanamide and 9-octadecanamide; lactams such as 2-pyrrolidinone, N-methyl-2-pyrrolidinone, N-ethyl-2-pyrrolidinone, N-butyl-2-pyrrolidinone, and other N-alkylated pyrrolidinones, 2-piperidinone and caprolactam; crotonaldehyde, saturated and unsaturated aldehydes and ketones such as cyclopentanone, cyclopentenone, methyl cyclopentenone, dimethyl cyclopenetenone, methyl furfural and hydroxymethyl furfural.

In one embodiment the one or more organic chemical products include but are not limited to carboxylic acids such as acetic, propionic, octanoic, dodecanoic, methylated butyric and valeric acids; lipid acids such as palmitic and oleic acids; phenol and cresol.

In another aspect, the present invention relates to organic chemical products produced according to the method defined in the first aspect.

In another aspect, the present invention relates to a method of producing dianhydromannitol or dianhydroglucitol from seaweeds in the phaeophyta, or from any alginate bearing material, by the method of the invention.

In another aspect, the present invention relates to the use of ethyl benzene or styrene obtained from the mixture produced according to the method of the invention for manufacturing polystyrene of biological origin.

In another aspect, the present invention relates to the use of dialkylated or polyalkylated pyrazines obtained from the mixture produced according to the method of the invention for manufacturing by oxidation pyrazine dicarboxylic acids or pyrazine poly carboxylic acids or anhydrides for the precursors of condensation polymers of biological origin.

In another aspect, the present invention relates to a method of producing alicyclic five-membered ketones from carbohydrates, by the method of the invention.

In another aspect, the present invention relates to a method for producing pyrazines and lactams in the presence of other materials from microalgae comprising
(i) heating an aqueous slurry of microalgae in a pressure vessel at a temperature of about 330° C. to about 450° C. to produce an organic phase and an aqueous phase, and
(ii) separating the pyrazines and lactams from the mixture.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

Further aspects and advantages of the present invention will become apparent from the ensuing description which is given by way of example only.

DETAILED DESCRIPTION OF THE INVENTION

In general, the present invention relates to a process where an aqueous slurry comprising biomass, water and a phosphate is optionally pH adjusted to between pH 3-11 and the slurry is heated to a temperature of about 150 to about 500° C. under sufficient pressure to either maintain water in the liquid state if the temperatures are sub-critical or to exceed the supercritical pressure if the temperatures are supercritical. The biomass may comprise microalgae or any biomass that is primarily protein or lipid based, or it may be carbohydrate based, such as macroalgae or any cellulose-based biomass, or any mixture thereof. Temperatures of approximately 150° C. produce limited amounts of extractable organic chemical products; temperatures of about 200° C. will usually lead to the additional production of lipid acids; temperatures above approximately 250° C. lead to the additional production of nitrogen-based heterocycles from proteins; and temperatures above 300° C. lead to oxygenated products and aromatic hydrocarbons. Without wishing to be bound by theory, it should be understood that these temperatures are guidelines only for times in the tens of minutes range, and lower temperatures and longer times may achieve similar outcomes, while higher temperatures will lead to shorter reaction times, and at supercritical temperatures, different product ratios. The resultant mixture may be extracted or separated to produce materials that are valuable as chemicals, chemical feedstocks, or for subsequent conversion to fuel.

The addition of about 5% by weight phosphate permitted faster reactions leading to the products of this invention, while in the absence of added phosphate, under otherwise equivalent conditions, charring occurred leading to a rapid build-up of carbon and other solid material which required the reactor to be closed down and cleaned.

1. Definitions

When a chemical compound is named in the singular, it refers to that specific compound, thus pyrazine would refer to 1,4-diazabenzene. When the term is used in the plural, it refers to the entire set of structures with that structural element, thus pyrazines would include all molecules with the pyrazine structure, including but not restricted to molecules with any substitution such as methylation or any molecule within which the pyrazine structure can be found. If a statement is made involving such a set of molecules, such as the term pyrroles, the subsequent use of a specific molecule that is an element of that set of molecules, such as indole, does not in any way contradict the generality of the previous statement, but should be taken as a special example or a special case.

The term "algal biomass" as used in this specification means any composition comprising algae. The algal biomass may be partially de-watered, i.e. some of the water has been removed during the process used to harvest the algae, for example during aggregation, centrifugation, micro-screening, filtration, drying or other unit operation The algal biomass may also comprise dried algae. The raw material may also comprise additional biomass derived from other sources and may therefore implicitly comprise, without express statement of, "other contributing biomass" which may be biomass derived from other sources, such as for example biomass from cellulosic sources.

The term "biomass" as used in this specification means any material of biological origin, including that having undergone processing, but not including that which as been fossilized.

The term "comprising" as used in this specification means "consisting at least in part of"; that is to say when interpreting statements in this specification and claims which include "comprising", the features prefaced by this term in each statement all need to be present but other features can also be present. Related terms such as "comprise" and "comprised" are to be interpreted in similar manner.

The term "lactam" as used in the specification refers both to a lactam or its amino acid precursor, i.e. a material capable of producing the lactam. The specific chemical lactam is similarly either the lactam or its precursor. The reason for this is that the method of identification, gas chromatography/mass spectrometry, and our method of isolation, namely final distillation would convert any precursor amino acid into a lactam, and the lactam is the desired structure of economic interest.

The term "pressure vessel" as used in this specification means a container that is capable of holding a liquid, vapour, or gas at a different pressure than the ambient atmospheric pressure.

"Wastewater" includes fresh or saline water, effluent from sewage treatment plants and water from facilities in which domestic or industrial sewage or foul water is treated.

The term "yield" as used in this specification refers to the weight of the recovered material as a fraction or percentage of the estimated dry weight of biomass, even though the sample actually used was never dried. The original dry weight is estimated based on actual dry weights achieved with equivalent samples.

2. Feed Materials

Biomass can have a variety of components. These components may include:
(a) Lipids. These are characteristically straight chain hydrocarbon fatty acids, most commonly bound in triglycerides, but the acid fragments are also found in phospholipids, glycolipids and lipoproteins.
(b) Hydrocarbon-based components. On land plants, these are the terpenes, but terpenes and related materials, such as steroids, steroid precursors, etc are also found in marine algae, and while in land plants these are frequently oxygenated, in marine plants they may also form sulphides or halogenated (usually brominated) species.
(c) Protein. This comprises polymers based on 21 amino acids that form a number of polymers with a large variety of properties simply through the variation in the ways they are combined.
(d) Nucleic acids. These are polymers based on phosphate diesters of ribose or 2-deoxyribose, which are substituted through C-1 with nucleotides.
(e) Carbohydrates. These are based on sugars, and are usually found as polymers.
(f) Phenolics. These are polyphenols, such as lignins, tannins, etc.
(g) Miscellaneous functional materials, such as chlorophylls.
(h) Water. As a main component of biomass, the presence of water affects its processing as it requires a large amount of energy to remove it.

The biomass used in the processes of the invention may include any type of biomass. For example, marine or fresh water micro algae, marine or fresh water macro algae, seaweed, biomass derived from woody or non-woody land based plants, or combinations thereof. Biomass from woody or non-woody land based plants may include whole crops or waste material selected from the group comprising but not limited to cellulose, lignocellulose, any grasses (for example, straw), soft wood (for example, sawdust from *Pinus radiata*), any hard wood (for example, willow), any scrub plant, any cultivated plant, corn, maize, switchgrass, rapeseed, soybean, mustard, palm oil, hemp, willow, jatropha, wheat, sugar beet, sugar cane, miscanthus, sorghum, cassaya, or any combination of any two or more thereof.

In one embodiment, the biomass comprises algal biomass. The algal biomass for use in the process of the invention may comprise single-cell micro-algae or macro-algae, and may be harvested from any source, such as bioreactors, aquacultured ponds, waste water, lakes, ponds, rivers, seas etc.

In one embodiment, the biomass may comprise slurried seaweed. While microalgae may be the fastest growing plants, macroalgae, particularly *Macrosystis pyrifera* and other members of the Laminariales grow rapidly and grow to very large and readily harvestable sizes, and there are large masses of other seaweed that are in the Phaeophyta such as, but not restricted to, members of the Fucales and the Durvillaeales. Similarly, seaweed from the Chlorophyta, such as Ulva, can also grow rapidly under nutrient rich conditions to give material that is otherwise difficult to get rid of.

In one embodiment, algal biomass comprises micro-algal biomass. Any endemic or cultured microalgae may be used, as a mixed culture or a monoculture, and there are hundreds of thousands of microalgal species. Examples of suitable microalgae include but are not limited to microalgae of Division Cyanophyta (cyanobacteria), microalgae of Division Chlorophyta (green algae), microalgae of Division Rhodophyta (red algae), microalgae of the Division Chrysophyta (yellow green and brown-green algae) that includes the Class Bacillariophyceae (diatoms), microalgae of Division Pyrrophyta (dinoflagellates), and microalgae of Division Euglenophyta (euglenoids), and combinations thereof. Examples of Chlorophyta include but are not limited to microalgae of the genera Dictyosphaerium, Micractiniumsp, Monoraphidium, Scenedesmus, and Tetraedron, or any two or more thereof. Examples of cyanobacteria include but are not limited to microalgae of the genera Anabena, Aphanizomenon, Aphanocapsa, Merismopedia, Microcystis, Ocillatoria, and Pseudanabaena, or any two or more thereof. Examples of Euglenophyta include but are not limited to Euglena and Phacus. Examples of diatoms include but are not limited to Nitzschia and Cyclotella. Examples of dinoflagellates include but are not limited to Peridinium.

In one embodiment, the biomass is cellulose.

3. Biomass Slurries

The biomass is fed as a slurry in a fluid, the fluid usually being water. The amount of water must be sufficient to permit the slurry to be pumped or otherwise moved. The amount of water must also be sufficient to ensure an adequate volume of fluid phase in a subcritical reaction, or to maintain the required pressure in a supercritical reaction. Therefore the amount of water required depends on the final temperature and pressure used, the pumping equipment used, and the reactor configuration. It will also depend on the nature of the biomass, as some biomass, particularly dried biomass, absorbs water.

The more dilute the biomass slurry, the more energy is wasted heating water. Therefore, higher concentrations of algae are desirable. In the case of microalgae, the lower practical concentration of microalgae is about 1 to 2% by weight. From an operational point of view, for a continuous flow process about 50% by weight of microalgae is an upper limit and about 80% by weight for a batch reactor with proper allowance for headspace. The actual concentration used will be influenced by cost, including the cost of concentrating the microalgae prior to use in this invention, and this invention applies to all such concentrations. A worker having ordinary skill in the art will be able to select the appropriate biomass concentration having regard to that skill Biomass from different sources may be mixed, e.g. cellulosic material with microalgae. Biomass may have been pretreated, e.g. chemical pretreatment, hydrolysis, size reduction, etc.

In various embodiments, the biomass concentration of the slurry comprises about 1, 2, 3, 4, 5, 6, 7, 8, 9, 10, 15, 20, 25, 30, 35, 40, 45, 50, 55, 60, 65, 70, 75 or 80% by weight and useful ranges may be selected between any of these values (for example, about 1 to about 10, about 1 to about 20, about 1 to about 30, about 1 to about 40, about 1 to about 50, about 1 to about 60, about 1 to about 70, about 1 to about 80, about 10 to about 30, about 10 to about 40, about 10 to about 50, about 10 to about 60, about 10 to about 70, or about 10 to about 80% by weight).

4. Heating

The biomass/aqueous slurry may be heated at any temperature of about 150° C. to about 500° C. under pressure, including at least about 150, 160, 170, 180, 190, 200, 210, 220, 230, 240, 250, 260, 270, 280, 290, 300, 310, 320, 330, 340, 350, 360, 370, 374, 380, 390, 400, 410, 420, 430, 440, 450, 460, 470, 480, 490 or 500° C., and useful ranges may be selected between any of these values (for example, about 200 to about 450, about 300 to 380, about 340 to about 380, and about 370 to about 450° C.).

There are, two preferable ranges of temperature that give approximately equivalent yields, but of different materials. In one embodiment the biomass is heated at a temperature of from about 300° C. to about 374° C., preferably from about 340° C. to about 374° C. if the reaction is intended to take place under subcritical conditions. In one embodiment the method of the invention is for the manufacture of aromatic compounds at subcritical temperatures.

In another embodiment the biomass is heated at a temperature of from about 374° C. to about 450° C. if the reaction is intended to take place under supercritical conditions.

The biomass may be heated for a time period of about 0.5 seconds to about 12 hours. In various embodiments the biomass may be heated for about 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 550, 600, 650 or 700 minutes, and useful ranges may be selected between these values (for example, about 1 to about 60, about 1 to about 120, about 1 to about 180, about 1 to about 240 minutes, about 5 to about 60, about 5 to about 120, about 5 to about 180, or about 5 to about 240 minutes).

In one embodiment the time period is preferably about 5 minutes to about 3 hours or about 5 minutes to about 60 minutes. As a general principle, the lower the chosen temperature, the longer the heating time required to achieve a specific objective. Accordingly, the heating time can be selected for convenience. The overall yield increases progressively with time, at least to 30 minutes, with the greatest increase up to 10 minutes, but the increased yield after 10 minutes sometimes arises through the formation or extraction of higher molecular weight products, hence shorter times may be more desirable if the volatile components are more desired.

At a given temperature, the relative product distribution is a function of time, therefore there is no optimum reaction time other than in terms of which are the desired products. As a general rule, longer times favour condensation reactions, hence the products are less volatile, more viscous, and generally are more likely to require significant downstream processing. Shorter times may be preferred, even if total processing of microalgae is not achieved, in order to maximize the production of higher value products.

In another embodiment the biomass is heated for a first period at a first temperature for about 1 to about 120 minutes or more and for a second period at a second temperature for about 1 to 120 minutes or more, where each of the first and second periods may be independently selected from at least about 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 110, 120 minutes, and useful ranges may be selected between these values (for example, about 1 to about 15, about 1 to about 30, about 1 to about 45, about 1 to about 60, about 1 to about 75, about 1 to about 90 or about 1 to about 105 minutes). In various embodiments the first temperature is about 150 to about 373° C., about 300 to about 373° C. or about 340 to about 373° C. In various embodiments the second temperature is about 374 to about 500 or about 374 to about 450° C.

5. Pressure Treatment and the Pressure Vessel

The pressure generated is dependent on the amount of water present, as this water provides the pressure. There must be sufficient water present to provide a liquid phase if subcritical, and the appropriate water partial pressure if supercritical, as otherwise excessive charring may occur.

Additional pressure may be applied to achieve certain objectives, e.g. increasing the pressure generally increases the yield of aromatic products.

In various embodiments, the pressure vessel which may be utilised for the processes of the present invention may be a tank, a batch reactor, a continuous reactor, a semi-continuous reactor of stirred-tank type or of continuous staged reactor-horizontal type or vertical-type, or alternatively of a tubular-type or tower-type reactor. A fluidised-bed or slurry-phase reactor may also be employed. Such vessels and reactors may be further specified as appropriate for use with the type or phase of catalysts and/or reagents which may be used.

Accordingly, in one embodiment the aqueous slurry is heated under autogenous pressure in the pressure vessel. In various embodiments the pressure in the pressure vessel is about 1, 2, 3, 4, 5, 6, 7, 8, 9, 10, 15, 20, 25, 30 or 35 MPa and useful ranges may be selected between any of these values (for example, about 1 to about 30, about 5 to about 25, or about 10 to about 25 MPa).

6 Catalysts

In the process of the invention a phosphate catalyst is added to the biomass prior to heating. The phosphate may be either soluble or insoluble in water and may be added as a specific phosphate, such as trisodium phosphate, or it may be formed in situ. For example, an ammonium phosphate may be formed by adding phosphoric acid, then adding sufficient ammonia to form the desired phosphate anion, which can be monitored by measuring the pH. Thus if using ammonium dihydrogen phosphate, ammonia would be added until the pH was approximately 6. Calcium dihydrogen phosphate could be prepared either by adding calcium hydroxide to phosphoric acid, or any acid to calcium phosphate until the pH is approximately 6. Similarly, an insoluble phosphate could be prepared by adding a soluble phosphate and a suitable counterion, and adjusting the pH. For example, if phosphoric acid is added, followed by sufficient slaked lime, or a soluble calcium salt, followed by any alkali, a precipitate is obtained with pH>7. For the purposes of this invention, the precipitate so obtained will be termed calcium phosphate, although in practice it may well be calcium hydroxylapatite. Suitable cations to act as counterion for the phosphate species may comprise monovalent cations including but not restricted to sodium, potassium, ammonium or hydrogen; divalent cations including but not restricted to magnesium, calcium, strontium, barium, zinc, copper, nickel, ferrous, manganous; or trivalent cations including but not restricted to aluminium, chromic and ferric; or any combination of any two or more thereof.

The exact choice of counterion, or the method of adding it, is dependent on the desired products to be made, such possible variation being illustrated by example. The nature of the products are also dependent on the amount of catalyst, at least in some cases, hence the amount of catalyst used, or which catalyst is used, may be influenced by the demand for given products at the time.

The presence of the phosphate catalyst influences the composition of organic chemical products obtained in step i). Depending on the temperatures and heating times used, the process will produce a range of organic chemical products that may be useful without further purification, or more likely will be further separated into chemical families or individual compounds for other uses.

In one embodiment the aqueous slurry comprises at least about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30% by weight of one or more phosphate catalysts and useful ranges may be selected between any of these values (for example, about 1 to about 5, about 1 to about 10, about 1 to about 15, about 1 to about 20 or about 1 to about 30% by weight).

7. Separating the One or More Organic Chemical Products from the Mixture

Optionally, before separating one or more organic chemical products, the mixture resulting from the heat and pressure treatment step may be filtered to recover solids, including catalyst or reagent materials.

Figure 1:
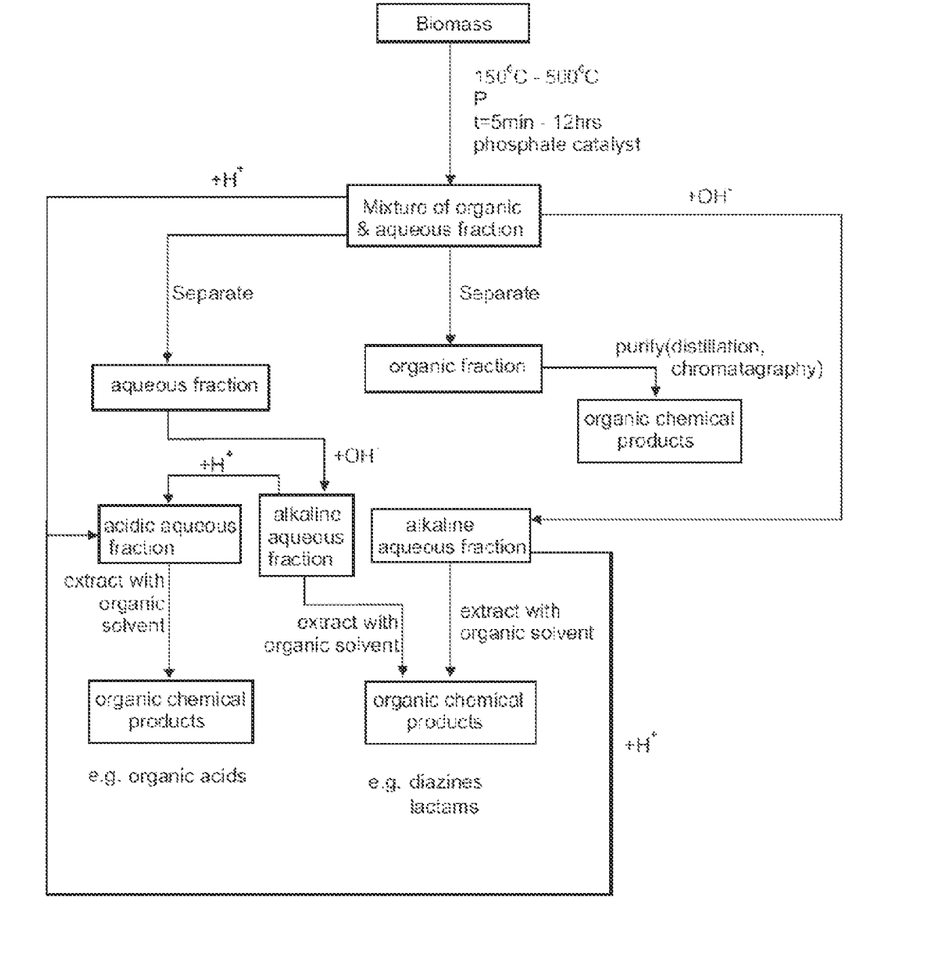
FIG. 1 is a flow diagram showing the general steps of some embodiments of the method of the invention.

One or more organic chemical products can be separated from the mixture resulting from the heat and pressure treatment step by any means known in the art including decanting the organic fraction off the aqueous fraction, or extracting the fractions with one or more organic solvents. Options for extracting the aqueous fraction and organic fraction are described below and one general scheme is shown in FIG. 1.

In one embodiment, the aqueous fraction or the biomass residue may be extracted with one or more organic solvents to obtain organic material adhering to the biomass residue or forming a colloidal distribution in the aqueous fraction or dissolved in the aqueous fraction.

Extraction may be carried out using any organic solvent or combination of organic solvents that are insoluble in water. Examples include, but are not restricted to, light hydrocarbons such as light petroleum spirit, pentane, methylene chloride and other halogenated hydrocarbons, toluene and other aromatic hydrocarbons, ethyl acetate and other esters, diethyl ether and other ethers, and also materials such as propane and butane that are gases at normal temperatures but can be liquids under suitable pressure, if such pressure was applied.

In one embodiment, the organic fraction may be simply separated from the aqueous fraction to provide an organic chemical product that may be used as a fuel precursor. In another embodiment the organic fraction may be further separated into one or more organic chemical products that may be useful in applications including but not limited to biofuel production, or providing feedstock for other chemical processes.

In one embodiment, the further separation step may be a distillation step, either single or multistage, or by flashing and condensing volatiles from the reaction. The distillation step may be prior to extraction, in which case water is also distilled. Various fractions obtained by extraction or partitioning may also be distilled.

Separation of organic chemical products can be achieved by acidifying or alkalysing the aqueous fraction prior to extraction into an organic solvent, or by extracting a solution of organics in an organic solvent with aqueous acid or alkali. For example, acidification of the aqueous fraction will protonate any organic acids present, allowing them to be subsequently extracted from the aqueous fraction with organic solvents. FIG. 1 depicts options for acidifying or alkalysing the aqueous fraction, followed by extraction with an organic solvent. In one embodiment the aqueous fraction is alkalised and the resulting alkaline aqueous fraction is extracted with organic solvent to produce nitrogen bases. Acidification and basification may be carried out in any order.

Organic chemical products can also be obtained from the aqueous fraction. If the aqueous fraction is acidified and extracted with solvent such as pentane or methylene chloride carboxylic acids are obtained, mainly acetic, propionic, and methylated butyric and valeric acids. These products are likely obtained by deamination of amino acids, and some lipid acids, including palmitic and oleic acids. Phenol and cresol were also found, probably because the ammonia solutions were of a pH suitable for partial dissociation. Lactams such as 2-pyrrolidinone may also dissolve in the aqueous fraction, in which case they may cause some organic materials such as aromatic hydrocarbons to accompany them.

If the aqueous fraction is made basic, extraction will obtain organic bases. Since some bases include piperidine, the pH should be raised to 12 to extract this material. Lactams will also be extracted with the organic bases.

The order of pH variation is not critical, and the first extraction may be carried out at either high or low pH, or if desired, at an intermediate pH to gain a particular separation. For example, an initial extraction at pH 7 would lead to a fraction containing hydrocarbons, pyrazines, lactams, etc, but leave both carboxylic acids and saturated amines in solution.

Changing the pH of the organic fraction may allow some organic chemical products present in the organic fraction to be able to be extracted into an aqueous solution. For example, if an acid solution that has been extracted is then made alkaline, diazines and similar organic chemical products can be extracted using organic solvents.

A higher yield of volatiles is often achieved at supercritical conditions, however there is often significant difference in the nature of the products, hence subcritical conditions may be desirable for specific products.

The organic chemical products obtained varied somewhat depending on the nature of the phosphate, but there were a number of products occurring at levels of approximately 2% that did not appear to change significantly with the phosphate catalyst used. One such compound was indole, and there were a number of higher boiling materials that appeared to contain pyrrole or pyrazine rings.

Certain fractions or chemical compounds may be separated and used as such, while the residue, which includes the higher boiling fraction, may be hydrocracked or otherwise treated by methods known to those practised in the art to convert them to more conventional fuels.

The organic chemical products obtained by the process of the invention may be separated into their chemical components using known purification techniques. These products can be used in many applications, including as a chemical feed stock for the synthesis of other chemicals. For example, the pyrazines can be used as flavour additives in the food industry, indoles may be used in the perfume industry, while the lactams have many uses, including as intermediates for polyamides or for inclusion as an amide in a condensation polymer, or as high boiling polar solvents. Amides produced by the process of the invention may be useful for subsequent conversion into solvents such as acetonitrile, or into surfactants and cationic detergents.

The separated chemical components produced by the process of the invention may also be used as chemical intermediates for the production of biopolymers. The use of lactams to make polyamides has been noted, but the oxidation of 2,5-dimethylpyrazine makes available a useful diacid, which may be a component of polyamides, while diols produced by the reaction with macroalgae may have value in polyesters. Such polymers, with high levels of nitrogen or oxygen may have particularly useful properties in terms of interaction with water and polar molecules that are difficult to get otherwise.

The following non-limiting examples are provided to illustrate the present invention and in no way limit the scope thereof.

EXAMPLES

1. Discussion of Examples

Determination of whether there was a catalytic effect was made on the grounds that the nature of the products changed. The products formed were determined by gas chromatography/mass spectrometry, and in some cases a chemical may have been present but not separated and clearly identified, in which case it is not reported.

Establishment of catalytic effects required a reference of microalgae processed without a catalyst. As shown by the examples, there were two basic approaches. Method 1 involved injecting a very small sample of slurry into a preheated reaction zone. This gave very rapid heat-up, but it also gave an erratic yield measurement, mainly because the amount of material injected was more difficult to determine. Method 2 involved relatively slow heating of a better defined mass of algae, but reactions that were nominally supercritical had also spent approximately an hour under general subcritical temperatures (300-374° C.) and probably ¾ hr between 200 and 300° C. Accordingly, these reactions should be viewed as supercritical reactions of subcritical products.

TABLE 1

Variability of product with respect to Phosphate Counterion [a]

| Counter-cation | T | % A | % P | % L | % D | % PA | Total |
|---|---|---|---|---|---|---|---|
| None [b] | 440 | — | — | 7 | 1 | — | 8 |
| None [b] | 350 | — | — | 9 | 24 | — | 35 |
| None [c] | 440 | 9 | 8 | 4 | 6 | 3 | 30 |
| None [c] | 350 | 15 | 8 | 6 | 4 | 2 | 35 |
| Sodium carbonate [b] | 400 | 12 | 4 | 2 | 4 | 7 | 29 |
| H | 400 | 6 | 2 | 2 | 3 | — | 13 |
| $Na_3$ | 440 | 22 | 3 | 7 | 12 | 3 | 47 |
| $Na_3$ | 350 | 5 | 9 | 15 | 10 | 1 | 40 |
| $Na_2H$ | 400 | 15 | 4 | 8 | 9 | 2 | 38 |
| $Na_2H$ | 350 | 12 | 8 | 10 | 11 | 4 | 45 |
| $NaH_2$ | 400 | 19 | 5 | 5 | 5 | 4 | 38 |
| $NaH_2$ | 350 | 10 | 7 | 7 | 10 | 2 | 36 |
| $NH_4H_2$ | 400 | 14 | 1 | 5 | 8 | — | 28 |
| Conc. $(NH4)_2H$ | 400 | 11 | 33 | 0 [d] | 3 | 4 | 51 |
| $(NH_4)_2H$ | 400 | 28 | — | 2 | 5 | 18 | 53 |
| Fe | 400 | 6 | 3 | 8 | 4 | 3 | 24 |
| Fe | 350 | 17 | 8 | 1 | 2 | 2 | 30 |
| Al | 400 | 13 | 10 | 11 | 4 | 3 | 41 |
| Al | 350 | 18 | 6 | 6 | 6 | 3 | 39 |

A = aromatics, P = pyrazines, L = Lactams, D = material suitable for direct use as diesel or biodiesel, and includes fatty acids and amides, PA = potential oxygenated petrol additives; Total represents the sum of the percentages of immediately marketable materials
[a] Percentages are percentages of compounds in recovered oil
[b] Phosphate not added, method 1
[c] Phosphate not added, method 2, overall yields approaching twice those of method 1.
[d] Not detected, but aqueous layer not worked up.

Table 1 illustrates the potential to vary the product distribution as a consequence of varying the nature of the phosphate species and compares them with the absence of phosphate. When employing the rapid reactions of method 1 without phosphate being added, the overall yields were approximately 10%, while the solids varied from 15% to 30%, with the yield of recovered solids invariably being greater than the yield of oil. The relatively high yield of diesel components in the subcritical reaction arises from a high level of fatty acids and their amides, which are included because they could be converted to standard biodiesel.

Many of the phosphate reactions in Table 1 are at alkaline pH, so a reaction was also carried out using sodium carbonate. There are generally low levels of nitrogenous compounds, together with reasonable levels of aromatic compounds, and the highest amount of oxygenated petrol additives. Various runs were tried employing different times with method 1, at 380° C. and 440° C. At the higher temperature a relatively constant product ratio was observed, but at the lower supercritical reaction, a similar distribution was only reached after 40 minutes, the shorter times giving less aromatic compounds. One run employing method 2, where the heat-up times were longer, gave a yield of approximately 30% oil, and only 5% of recovered solids, with products similar to those of Method 1 at 440° C.

Reactions carried out in the pilot plant continuous reactor (Method 3) led to significant carbonization in the absence of added phosphate.

The use of phosphates significantly increased the overall yields of materials, and also increased the yields of desirable materials as shown by Table 1. Further, the amounts of given products could be varied significantly by altering the counterion to the phosphate. The amount of aromatics produced can be varied by almost a factor of 4.5, and aromatics are favoured by higher pH, possibly because at low pH there may be further reactions, as indicated by the higher yields at lower temperatures for ferric and aluminium phosphate. Similarly, the products from the phosphoric acid reaction appeared to be mainly high-boiling and indeterminate. The highest level of aromatic compounds we recorded was with diammonium hydrogen phosphate, at pH 8.5, where there will be some triammonium phosphate. The diesel precursors follow a similar pattern, except for the diammonium hydrogen phosphate, where there was a relatively low yield of diesel materials. The pyrazines appear to be inhibited by high pH, but are greatly enhanced by the presence of more concentrated ammonium phosphate species. Lactam production appears to be favoured at lower pH and lower temperatures. The oxygenated petrol additives are relatively unaffected by conditions, except again the diammonium hydrogen phosphate gave surprisingly high levels, including significant amounts of oxygenated species not positively detected in the other reactions.

The results we obtained were consistent with the concept that the ammonia so produced could be an important reagent, and amides, such as acetamide and the amide of hexadecanoic acid, were produced in many reactions. Lactams, such as 2-pyrrolidinone and 2-piperidinone, were also formed. Interestingly, N-alkylated derivatives, methyl to butyl, of 2-pyrrolidinone were formed in some, but not all reactions, while 2-piperidinone was seemingly immune to N-alkylation.

The use of phosphoric acid as a catalyst gave a total of 43% yield of exractibles, but most of these were unidentifiable by our methodology, and further, 15% were in the aqueous fraction, and apart from acetic and propionic acids did not appear to be the usual carboxylic acids, or if they were, they were not resolved from other contaminants by gas chromatography. There were also modest amounts of lactams present, and with such a yield, the remaining material may be suitable as a raw material for further processing, such as hydrocracking for fuel.

When trisodium phosphate was used as a catalyst, the yields of oil in supercritical reactions varied between 18-24% in the small reactor (Method 1), and between 24-35% for the bomb (Method 2). The aqueous fractions gave approximately 8% additional material, although when the pH was adjusted to 9.5, the yield in the aqueous phase increased to approximately 17%. The sodium phosphate was of particular interest for synthetic fuel because under supercritical conditions it gave enhanced yields of aromatic hydrocarbons, mainly toluene and ethyl benzene and styrene, and indeed the yield of ethyl benzene was sufficient that it could be selectively isolated for the production of polystyrene made from biological sources. Also relatively enhanced were the higher molecular weight linear alkanes and alkenes, although they still do not account for all that is expected of the lipid fraction. The nitrogenous material appears to end up mainly in the aqueous phase, in the form of amides, pyrazines, pyrroles and lactams, the latter being of commercial interest as polar solvents or polymer precursors. In the subcritical reactions the yield of aromatic hydrocarbons was much lower while the yield of lactams was substantially higher, and the yield of pyrazines somewhat higher. Thus if this catalyst were to be used, and if petrol components were desired, then supercritical temperatures are desirable, however if the desired products are the nitrogen heterocycles, subcritical temperatures are preferred.

The dependence of yield on concentration is shown in Table 2 (Example 8). The difference in yield between 20% and 30% algal concentration is, in our view, a consequence of higher concentrations of catalyst, and in other respects, the yields are very similar. When the concentration was taken to 70% algae, there was a drop in yield of oil, and a significant increase in resultant solids, and this was, in our opinion, a consequence of there being less water. As the fraction of water drops, there is a point where there is insufficient to properly maintain the required vapour pressure. The effect of this will be ameliorated by a slow heat-up (as more reaction occurs at lower temperatures where there is enough water) but it will also be dependent on the design of the equipment. Our conclusion is that the concentration of microalgae is not critical provided there is sufficient water for the headspace, however the degree of mixing probably is.

A change of pH will change the nature of the phosphate anion, and it also changed the yields, and to some extent the nature of the products. The highest yield of material we obtained under subcritical conditions (53% oil, 10% aqueous extract) was obtained with disodium hydrogen phosphate as a catalyst. When sodium dihydrogen phosphate was used, the yield was 32.5% oil, and 5.2% aqueous extract. Accordingly, the yields of products appear to be highest when the reactions are carried out in the pH range 7-8. Sodium dihydrogen phosphate increased the yield of aromatics at supercritical temperatures compared with subcritial temperatures, but the diesel fraction followed the opposite trend. In part this may be because the diesel fraction listed in Table 1 includes some highly unsaturated material, and amides which would required further processing to be used as diesel, and which presumably react further at supercritical temperatures.

The use of ammonium dihydrogen phosphate as a catalyst tended to give lower yields, thus ammonium phosphate at pH 6.5, although a different reaction, with an increase in the phosphoric acid to bring the initial pH to 5.5 gave a yield of 29% oil and 7% aqueous extract. However, the products were also different. The predominance of amides from the aqueous acids at higher pH is probably due to the higher levels of ammonia present, however the presence of pyridines and the higher yield of lactams indicates the underpinning chemistry may be accelerating different paths. At lower pH, however, the yield of aromatics and cyclic ketones increased significantly, and there was almost a full range of deaminated amino acid residues, except again there was an unexpected surplus of butanoic acid.

An increase in the amount of ammonium phosphate, and an increase in the pH, led to a somewhat different product ratio, and some new products under supercritical conditions. The amount of nitrogen containing products increased significantly, and this method gave the maximum yield of pyrazines, but it also produced pyridine and pyrimidines. The aqueous phase was not analysed. However, if the pH was increased slightly, but the overall concentration was reduced, the amount of nitrogenous material was significantly reduced. The yield of oil was 31.5%, while a further 12% was obtained from the aqueous phase. The oil was particularly rich in aromatic compounds and the low-boiling oxygenated species that should be useful for high octane petrol, while the aqueous fraction largely contained (at least amongst the identifiable compounds) deaminated amino acids. Accordingly, if the objective is to prepare nitrogenous material such as pyrazines with ammonium phosphate, increasing the amount of ammonium phosphate or decreasing the pH is desirable. If the objective is to produce materials low in nitrogen, then the solution should be in the higher pH range, with enough ammonium phosphate to catalyse the reactions, but without an excess.

The example using calcium phosphate is an example of a procedure involving the precipitation of an insoluble phosphate onto microalgae and is of interest because the product range is somewhat different, with pyrroles, lactones and N-methyl succinimide being formed. The precipitation technique, of course, will also precipitate soluble phosphate from within the microalgae, and the different nature of the products illustrates the catalytic effects. The production of aromatic compounds is much lower than for the sodium phosphate at similar pH, as is the production of pyrazines, however the most interesting point is the large-scale production of palmitic and oleic acids and their amides. Given that the feedstock came from a large volume collected at the same time, and that the same source was used for the runs involving sodium phosphate, then it is clear from the absence of further materials present at appropriate levels that in the latter case the lipid fraction must have reacted further to form a material that was not volatile. The products at 250° C. were essentially the same as those at 350° C., although proportionately different. The total acids and amides, while proportionately similar within this set, totalled just under half the products, although the overall yield was only half that of the reaction at 350° C. This indicates that the reactions with the lipids to yield acids is one of the first reactions to occur.

The supercritical reaction with ferric phosphate gave an oil in 28.4% yield, and the aqueous fraction gave a further 6.7% yield. The oil was somewhat different from other oils, and an unusually high fraction of it was unidentifiable. However, it was noted that in the oil fraction, the amount and number of identifiable compounds containing nitrogen was remarkably low, and in the aqueous fraction the only significant materials were carboxylic acids. The implication is that ferric phosphate is a useful deamination catalyst for amino acids. Additionally, there was a very high fraction of butyric acid, and it is most unlikely this came from a four or five carbon amino acid. The implication is that the ferric phosphate has also reacted with some of the carboxylic acids (or amino acids or small peptide components) and formed higher molecular weight materials from them. The subcritical reaction gave an oil yield of 42%, together with 9% in the aqueous phase that was recovered following acidification. Of particular interest is the high yield of dimethyldisulphide. Since the sulphur has to go somewhere, the implication is that this catalyst may be desirable for producing lower sulphur containing fuels. Not only that, but it also produces relatively fewer nitrogen containing materials, at least amongst those that are identifiable, and with the high yield of aliphatic acids in the aqueous phase, it would seem that this is a useful catalyst for deaminating amino acids. Finally, the high yield is under relatively mild conditions and shorter reaction times, in this case 30 minutes.

The supercritical reaction with aluminium phosphate gave an oil in 34.6% yield, and the aqueous fraction gave a further 8.7% yield. The reaction had similarities with the ferric phosphate reaction, but there were also marked differences, for example the oil had a relatively high yield of xylene. In the aqueous phase, the number of carboxylic acids was much reduced, however there was little or no acetic acid, although there was acetamide. There was also a rather high yield of butanoic acid. Further, while the yield of 2-pyrrolidinones was much lower than with most other phosphates, the percentage of 2-piperidinone was unusually high. The subcritical reaction gave an oil yield of 22.7%, and the aqueous fraction gave a further 13.2% if reacted for 1 hr, but 41.4% yield of oil and 8.3% yield in the aqueous fraction if reacted for half an hour. This indicates that the catalyst is also destroying material by further reaction, however the reaction time is not especially critical. Some of the difference may arise from incomplete collection of the more volatile components, including the conversion to gas of some components in the longer run. As an example, the dimethyl sulphide was removed in the longer run, and no sulphur containing organic materials were found. (They could have been in inorganic ash.) There were also clear differences in the products, which are inexplicable other than by assuming further reaction occurred. One example is the complete removal of aromatic materials in the longer run, but their significant presence in the shorter run. These may have been incorporated in higher boiling but unidentified components (as pyrazines almost certainly were) but equally they may have been charred. The aqueous phase from the longer running subcritical reaction did not resolve well in the GCMS, and a considerable amount of material that was presumably mixed carboxylic acids was not positively identified. Accordingly, some of the differences noted in the aqueous fraction may be misleading, nevertheless there is clear evidence for a significant reaction occurring for the acetic acid, as this almost disappeared in the longer reaction.

One of the more interesting facts to arise from the aluminium phosphate catalysis is that the shorter milder reaction was optimum for producing fuel, thus longer reaction times and supercritical conditions gave poorer yields of aromatic components and diesel components. The supercritical reaction did produce more 2-piperidinone than the other reactions.

The ability to liquefy microalgae is not restricted to the green algae. A sample of blue-green algae from Lake Klamath (Oregon) was processed according to Method 2, using trisodium phosphate as a catalyst to give a yield of 45% oil. As can be seen from the example, the products were very similar to those of the green algae, including the possibility of producing approximately 14% of the oil as a raw material for styrene, a material of prime industrial use and for which there is no obvious alternative source from a renewable biological source.

The importance of this invention can be seen from the fact that this blue-green algae contained only 2% lipids. Such blue-green algae are generally regarded as noxious pollutants as they produce cyanotoxins, they form blooms if sufficient nitrogenous material is present to fertilize their growth, and since there are currently only occasional specialist uses for these algae there is a clear advantage in having a means to utilize large volumes of them. Clearly, our invention has a distinct advantage over other processes that are based on using the lipid content, or at least it offers the public a useful choice.

Reactions with cellulose were carried out with both ammonium hydrogen phosphate and trisodium phosphate, and one rather remarkable observation was that, apart from a small amount of methyl pyrazine and allowing for a pH difference, the reactions were similar for both ammonium and sodium phosphates in that the nitrogen from the ammonia did not participate. This implies that the nitrogen in the heterocycles found in the reactions involving microalgae all originated from the protein or nucleic acids. The reason why ammonium phosphate may have favoured the production of nitrogen heterocycles with microalgae would thus be because it inhibited the deamination of protein amino acids. The products from cellulose were mainly a range of ketones, mostly five-membered cyclic ketones, and these same materials were found in the reactions with microalgae. Since the cellulose was solely a carbohydrate, we consider that these products in the microalgae originated from carbohydrate components, and it also indicates that cellulose can be mixed with microalgae. It was also of interest to note that cellulose produced toluene in very small amounts under these conditions, but not ethyl benzene, which usually predominates with microalgae.

A reaction was also carried out with a dried, coarsely ground sample of Macrocystis pyrifera, an example of a macroalgae. A yield of 19.5% oil was recovered, plus a further 9% from the aqueous phase. The major carbohydrate component of Macrocyctis is sodium alginate, which is a salt of a polymer based on mannuroic and guluronic acids. This polymer requires counterions, and while sodium is the most common such ion, it also sequesters heavier ions. Further, as is often the case of macroalgae, this sample had encrustations of lime, and in this case a 37% yield of ash was also obtained. The yield will also be reduced compared with other biomass because in the absence of reducing agents, carbon dioxide must be eliminated from the uronic acids. The products from the oil fraction included the same cyclic ketones as was found from cellulose. Because the first reaction of the uronic acid is probably decarboxylation, and that some of these ketones are relatively hydrogen rich, these ketones probably arose through some recombination of fragments from the decarboxylated sugars. There were also components expected from a lipid fraction. The aqueous fraction, however, was of interest. There was a large amount of acetic acid, which presumably did not come from protein as there was very little other nitrogenous material present and the other acids from protein were not present, and there were also large amounts of dianhydromannitol and dianhydroglucitol. The latter would be expected to have come from gulose, in which case the dianhydroglucitol would be in the L-configuration. There is currently no simple procedure for manufacturing dianhydromannitol or dianhydroglucitol, and these materials would be of considerable interest as diol substitutes for hydrophilic polyesters.

2. Methods

Three different types of equipment were used.

2.1 Method 1

The reaction zone comprised a thin coil of stainless steel pressure resistant tubing within an oven, and this was connected to feed by means of a pump and appropriate valves, and to a collection point by means of appropriate valves. The tubing was preheated, and a slurry of microalgae (approximately 8% in water) together with whatever catalyst was added, was injected into the tubing at a predetermined temperature and pressure, left for a given reaction time, usually 30 minutes unless otherwise specified, then the sample was removed from the reaction zone by opening a valve to a collection point. To 25 g of the resultant cooled sample was added 25 mL of $CH_2Cl_2$, and the sample centrifuged at 1000 RPM for 15 minutes. The organic phase was then removed and the $CH_2Cl_2$ removed by evaporation to give oil. The remaining solids were dried at 105 C to give a total solids mass, and then ashed to give the organic and inorganic solids present.

2.2 Method 2

300 mL of a slurry of microalgae and catalyst in water was placed inside a stainless steel bomb, sealed, and brought to temperature by placing it in the oven. The bomb was allowed to heat, and it was found that if the reaction was to be supercritical, the bomb spent approximately ¾ hr between 300-370° C. The reaction was left for 30 minutes at supercritical temperatures, then withdrawn and allowed to cool. Accordingly, there are two heating profiles: a subcritical heating to 350° C. for 30-45 minutes, and a supercritical heating to material that has already had the subcritical treatment.

2.3 Method 3

The reaction zones comprised a 6 mm diameter, stainless steel pressure resistant tubing within an oven, and this was connected to feed by means of a pump and appropriate valves. The tubing was connected to a collection point by means of appropriate pressure reducing control and valves. The tubing was preheated, and a slurry of microalgae (approximately 8% in water) together with whatever catalyst was added, was injected under continuous flow into the tubing at a predetermined temperature and the system was controlled to maintain the desired reaction pressure. The residence time (reaction time) at reaction temperature for the microalgae slurry was set and controlled by using a combination of the length of tubing in the reaction zones and the flow rate of feed slurry into the reactor. The reacted mixture passed from the reaction zones and was quenched in an exit heat exchanger before the pressure was reduced through the pressure control device. The depressurised fluid was connected to a collection vessel by tubing and appropriate valves. The flow rate range of the reactor was 10 to 50 liters per hour.

2.4 Work-Up and Analysis

The total sample was filtered slowly through the Soxhlett thimble to remove the aqueous phase. The subsequent aqueous phase was extracted with 3×100 mL of CH2Cl2. The organic extracts were combined and then used as the extracting solvent in the Soxhlett. The extractor was run until the solvent in the upper barrel was clear. The CH2Cl2 was then distilled to give oil. The remaining aqueous phase was then acidified to pH 1 by addition of $HNO_3$ and extracted with 4×50 mL of $CH_2Cl_2$. The organic phases were combined and the $CH_2Cl_2$ removed by evaporation to give the aqueous phase extracted oil.

Analysis of the extracts was carried out by gas chromatography/mass spectrometry on a Shimadzu GCMS QP2010 plus employing a RESTEK Rtx-5Sil MS 30M, 0.25 mm ID film thickness 25 um column. The injector temperature was 200° C., the split ratio was 10:1 and the interface temperature was 250° C. The oven temperature was programmed by being held at 50° C. for 1 minute, then the temperature was increased at 5° C./minute to 100° C., then 20° C./min to 300° C. and held for 4 minutes. Run time 25 minutes in a linear velocity (30 cm/sec) mode. The mass spectra covered the 40-450 amu range, and product identification was carried out with assistance of the National Institute of Standards and Technology 2005 and 2005s compound database versions, and by examination of the spectra. Not all products could be identified, but many such unidentified compounds could be partially classified e.g. containing long chain hydrocarbon fragments. In some cases the inability to identify a component arose because the GC resolution was incomplete, and the mass spectrum clearly arose from more than one component. In such cases, the material is not reported.

The relative yields reported below are those obtained by gas chromatography, hence are per centages of the volatile components, and in the case of the oils, the actual yield of the named materials must be reduced by the amount of non-volatile oil. Some of the materials present are known to condense with others on heating, and so a simple distillation will not overcome this difficulty. The yields of the aqueous phase materials are also per centages of the organic material present. Estimating these was difficult, but with method 2, where yields of oil were approximately 35% the mass of the algae, the yield of water-soluble organics was approximately the same. Thus on average, algal liquefaction produced something in the order of 7% by mass conversion to acetic acid (assuming a 20% average yield) by method 2, and other materials in the aqueous phase can be similarly evaluated. However, it should also be noted that these experiments were only approximately reproducible, and there were minor variations, presumably due to variations in the various variables, which remain insufficiently well-controlled.

Example 1

No Catalyst, Method 1

A slurry of 4% microalgae in water was subjected to the procedures of Method 1 to give yields of oil in the range 10-20%. The GCMS analyses of the relative compositions of the methylene chloride extract of the oil gave (as per centages of that extract that volatalized properly) were as follows:

Subcritical reaction, oil phase: p-cresol (1.6%), p-ethyl phenol (1%), N-methylsuccinimide (1.8%), 2-pyrrolidinone (0.9%), N-ethyl-2-pyrrolidinone (2%), 2-piperidinone (2.3%), pentadecene (2%), heptadecane (2.8%), hexadecanoic acid (13%), oleic acid (4.9%) hexadecanamide (1.8%), and some unidentified compounds.

Subcritical reaction, aqueous phase: acetic acid (25.4%), propionic acid (6.2%), 2-pyrrolidinone (5.8%), 2-piperidinone (6%), benzenepropanoic acid (1.4%) and some unidentified compounds.

Supercritical reaction, oil phase: N-methylsuccinimide (1.8%), 2-piperidinone (2.5%), heptadecane (1.2%), and some unidentified compounds.

Supercritical reaction, aqueous phase: acetic acid (29.4%), propionic acid (4.5%), N-methyl piperidine (13%), 2-pyrrolidinone (4.3%), 2-piperidinone (5.5%), benzene propanoic acid (1.4%) and some unidentified compounds.

Example 2

No Catalyst, Method 2

A slurry of 6% microalgae in water was subjected to the procedures of Method 2 to give yields of oil of 30%. The GCMS analyses of the relative compositions of the methylene chloride extract of the oil gave (as per centages of that extract that volatalized properly) were as follows:

Subcritical reaction, oil phase: toluene (1.8%), xylene or ethyl benzene (3.8%), styrene (3.4%), methyl pyrazine (2.3%), 2,5-dimethyl pyrazine (2.6%), trimethyl pyrazine (3.3%), 2-methylcyclopent-2-en-1-one (1.7%), 2,3-dimethylcyclopent-2-en-1-one (1.5%), butyrolactone (1%), 2-piperidinone (2.6%), pentadecene (2.5%), heptadecane (1.1%), oleiamide (2.1%), and some unidentified compounds.

Subcritical reaction, aqueous phase: acetic acid (22.3%), propionic acid (4.4%), butanamide (3.1%), 2-pyrrolidinone (2.5%), 2-piperidinone (4.1%), palmitic acid (6.5%), oleic acid (1.4%), and some unidentified compounds.

Supercritical reaction, oil phase: toluene (4.0%), ethyl benzene (6.9%), xtylene (1.7%), styrene (1.9%), methyl pyrazine (2.9%), 2,5-dimethyl pyrazine (3.0%), trimethyl pyrazine (2.3%), 2-methylcyclopent-2-en-1-one (2.2%), 2,3-dimethylcyclopent-2-en-1-one (1.9%), N-ethyl-2-pyrrolidinone (3.9%), indole (1.8%), 3-methyl indole (1.9%), pentadecene (1.4%), pentadecane (2.2%), and numerous unidentified products.

Supercritical reaction, aqueous phase extract: acetic acid (15.1%), N-methyl-2-pyrrolidinone (3.7%), 2-pyrrolidinone (<4.7%) and some unidentified compounds.

Example 3

Sodium Carbonate, Method 2—Comparative Example

A slurry of 6% microalgae in water containing 8% by weight of sodium carbonate was subjected to the procedures of Method 2. The GCMS analyses of the relative compositions of the methylene chloride extract of the oil (26% yield) gave (as per centages of that extract that volatalized properly) were as follows:

Supercritical reaction, oil phase: toluene (2.3%), ethyl benzene (9.4%), methyl pyrazine (1.3%), 2,5-dimethyl pyrazine (1.3%), trimethyl pyrazine (1.6%), 2-methylcyclopent-2-en-1-one (1.2%), 2,3-dimethylcyclopent-2-en-1-one (5.5%), p-cresol (2.6%), p-ethyl phenol (2.4%), N-ethyl-2-pyrrolidinone (2.1%), indole (1.9%), 3-methyl indole (2.3%), heptadecane (1.3%), hexadecanoic acid (1.6%), hexadecanamide (0.9%) and numerous unidentified products.

Supercritical reaction, aqueous phase extract (0.9% yield) following acidification to pH1: propanoic acid (4.8%), cyclopentanone (0.5%), butanoic acid (17.1%), 3-methyl butanoic acid (5.6%), 2-methyl butanoic acid (6.1%), 4-methyl pentanoic acid (12%), benzenepropanoic acid (13.1%), N-methyl-2-pyrrolidinone (4.6%), and some unidentified compounds.

Example 4

Phosphoric Acid, Method 2

A slurry of 6% microalgae in water and phosphoric acid (20 mL of 2M, to bring pH to 5.3) (21% by weight) was subjected to the procedures of Method 2. A GCMS analysis of a methylene chloride extract of the oil (27.8% yield) in the supercritical reactions gave (as per centages of that extract that volatalized properly)

Supercritical reaction, oil phase: toluene (3.3%), xylene (3.1%), probably pyridine (3.5%), trimethyl pyrazine (2.0%), 2,3-dimethylcyclopent-2-en-1-one (3.1%), N-ethyl 2-pyrrolidinone (2.3%), pentadecene (1.0%), pentadecane (1.0%), 3-eicosyne (1.1%).

Supercritical reaction, aqueous phase extract (14.9% yield): acetic acid 13.2(%), propanoic acid (3.6%), 2-pyrrolidinone (5.0%), 2-piperidinone (6.4%), benzenepropanoic acid (6.6%).

Example 5

Trisodium Phosphate, Method 2

A slurry of 6% by weight microalgae in water and trisodium phosphate (1.2 g in 300 mL) (7% by weight) was subjected to the procedures of Method 2. This was repeated many times in the supercritical region, and the yields varied from approximately 28%-35%, presumably due to sample variation. A subcritical run at 350° C. gave a 30% yield of oil. A GCMS analysis of the methylene chloride extracts of the oil gave (as percentages of that extract that volatalized properly):

Supercritical oil phase: toluene (5.9%), ethyl benzene (12.9%), styrene (2.7%), methyl pyrazine (1.9%), 2,5-dimethyl pyrazine (1.2%), trimethyl pyrazine (2%) 2,3-dimethylcyclopent-2-en-1-one (1.9%), butyrolactone (1%), p-cresol (2.7%), p-ethyl phenol (2.8%), 2-piperidinone (0.8%), 3-methyl indole (1%), undecene (0.8), pentadecene (5.7%), pentadecane (1.1), heptadecene (1.5%) heptadecane (2.9%), and numerous unidentified products.

Supercritical aqueous phase: acetic acid (8%) acetamide (5.8%), N-methyl acetamide (3.6%), butanoic acid (4.6%), 2-propylmalonic acid (3.4%), propanamide (1%), butanamide (3.5%), N-methyl 2-pyrrolidinone (4.7%), 2-pyrrolidinone (4.6%), N-methyl-2-piperidinone (3.8%), 2-piperidinone (7.7%). and numerous unidentified products.

Subcritical oil phase: ethyl benzene (3.3%), styrene (2.1%), methyl pyrazine (2.5%), 2,5-dimethyl pyrazine (2.5%), trimethyl pyrazine (3.6%) 2,3-dimethylcyclopent-2-en-1-one (1.4%), N-ethyl 2-pyrrolidinone (1.7%), 2-piperidinone (7.4%), indole (2.2%), pentadecene (2.2%), heptadecane (1.8%), tetramethyl hexadec-2-ene (3.2%), hexadecanamide (1.7%), oleiamide (1.6%) and numerous unidentified products.

Subcritical aqueous phase: acetic acid (3.2%), propanoic acid (3.5%), acetamide (8.4%), N-methyl acetamide (5.2%), N-ethyl acetamide (3%), butanoic acid (5.7%), 2-methyl butanoic acid (3.4%), butanamide (3.2%), piperidine (4.7%), 2-pyrrolidinone (8.3%), 2-piperidinone (18.5%). and numerous unidentified products

Example 6

Trisodium Phosphate with Sequential Work-Up 25.7 g algae plus 1 g of $Na_3PO_4$ (4% by weight) were heated in water (about 275 ml) at 440° C. for 30 minutes at a pressure of 23 to 25 MPa then cooled. The cooled sample from the pressure vessel was then washed with 4×50 mL aliquots of pentane. The combined organic phases were dried over magnesium sulphate and distilled to give 3.83 g of brown oil. GCMS analysis revealed the presence of dimethyl sulphide (7.8%), toluene (9.6%), ethylbenzene (19.1%), xylene (6.2%), and styrene (4.8%) as the major components.

The remaining sample was extracted with 4×50 mL $CH_2Cl_2$. The organic phase was set aside. The residual sample was then acidified to pH 1 and extracted with 4×50 mL of $CH_2Cl_2$ to remove the organic acids. The combined organic phases were dried over magnesium sulphate and distilled to give 0.83 g of a pale red oil. GCMS analysis revealed the presence of 2-methyl-propanoic acid (9.3%), n-butanoic acid (31.8%), 3-methyl-butanoic acid (7.5%), n-pentanoic acid (5.4%), 4-methyl-pentanoic acid (12.3%), and 1-methyl-2-pyrrolidinone (4.7%) as the major products.

The $CH_2Cl_2$ phase that had previously been set aside was washed with 4×50 mL aliquots of 2M $HNO_3$. The acidic layer was then set aside. The combined organic phases were dried over magnesium sulphate and distilled to give 5.579 g of a brown oil. GCMS analysis revealed the presence of n-hexadecanoic acid (13.1%), hexadecamide (3.3%), 9-octadecamide (2.0%), cyclopentanone (1.8%), 2,3-dimethyl-2-cyclopenten-1-one (2.1%), 4-ethyl-phenol (2%), and indole (1.2%).

The 2M $HNO_3$ layer from above was neutralized to pH 14 by the addition of NaOH, and extracted with 3×50 mL of $CH_2Cl_2$. The combined organic phases were dried over magnesium sulphate and distilled to give 0.43 g of a brown oil. GCMS analysis revealed the presence of pyridine (6.9%), 1,3-diazine (3.7%), methyl pyrazine (11.9%), 2,5-dimethyl pyrazine (12.5%), ethyl pyrazine (2.6%), trimethyl pyrazine (5.6%), 1-methyl-2-pyrrolidinone (8.0%), 1-ethyl-2-pyrrolidinone (4.0%).

The overall yield of recovered organic oils and chemicals for this reaction was 10.67 g (41.5%).

Example 7

Sodium Phosphate with pH Adjusted to 9.5, Method 2

A slurry of 6% microalgae in water and trisodium phosphate (1.2 5 g in 300 mL) (7% by weight) had its pH adjusted to 9.5 by the addition of small amounts of sodium hydroxide, and was then subjected to the procedures of Method 2 under supercritical conditions. A GCMS analysis of the methylene chloride extracts gave (as per centages of that extract that volatalized properly):

Oil phase: dimethyl disulphide (4.71%), toluene (6.9%), ethyl benzene (10.3%), styrene (1.6%), methyl pyrazine (2.9%), 2,5-dimethyl pyrazine (1.8%), trimethyl pyrazine (2.4%), 2-methylcyclopent-2-en-1-one (1.7%), 2,3-dimethylcyclopent-2-en-1-one (2.1° A), p-ethyl phenol (3.2%), indole (0.9%), 3-methyl indole (1.4%), pentadecene (1.9%), heptadecane (1.1%), hexadecanamide (1.1%) and numerous unidentified products.

Aqueous phase: acetic acid (8.9%), propionic acid (2.3%), 2-methyl propionic acid (3.5%), acetamide (1.5), butanoic acid (5.3%), 4-methyl pentanoic acid (4.4%), N-methyl 2-pyrrolidinone (5.3%), 2-pyrrolidinone (6.4%), N-ethyl 2-pyrrolidinone (1.4%), 2-piperidinone (10.6%). and numerous unidentified products.

Example 8

Variation of Algal Concentration

The procedure of example 4 was repeated using various concentrations of microalgae to determine the variation in yield of oil and solid residue. The results are summarized in Table 2

TABLE 2

Yield of oil as a function of algae concentration (Employing method 2)

| % Algae | Wt $Na_3PO_4$ (g/300 mL) | % oil | % solids |
| --- | --- | --- | --- |
| 20 | 3 (5% by weight) | 20 | 34 |
| 30 | 4.5 (5% by weight) | 37 | 31 |
| 75 | 4.5 (2% by weight) | 31 | 44 |

Example 9

Disodium Hydrogen Phosphate, Method 1

A slurry of 4% microalgae in water and disodium hydrogen phosphate (0.7 g in 300 mL) (6% by weight) was subjected to the procedures of Method 1. A GCMS analysis of the methylene chloride extracts gave (as per centages of that extract that volatalized properly):

Subcritical reaction, oil phase: pyrimidine (1.1%), methyl pyrazine (3.5%), 2,5-dimethyl pyrazine (2.2%), trimethyl pyrazine (1.3%) 2,3-dimethylcyclopent-2-en-1-one (1.9%), p-cresol (1.2%), N-methyl succinimide (1.6%), 2-piperidinone (4.1%), indole (1.8%), 3-methyl indole (0.6%), pentadecene (3%), heptadecane (0.8%), hexadecanoic acid (10.2%), hexadecanamide (2.4%), oleiamide (1.1%) and numerous unidentified products.

Supercritical reaction, oil phase: pyrimidine (4.4%), pyrrole (5%), N-ethyl pyrrole (0.6%), toluene (4.4%), ethyl benzene (0.7%), xylene (1.1%), styrene (0.6%), methyl pyrazine (7.3%), 2,5-dimethyl pyrazine (2.9%), trimethyl pyrazine (1.4%), cyclopentanone (1.3%), cyclopent-2-en-1-one (1%), 2-methylcyclopent-2-en-1-one (2.9%), butyrolactone (1.3%), 5-methyl-2-furaldehyde (0.7%), p-cresol (3.9%), p-ethyl phenol (1.2%), N-methyl succinimide (2.1%), 2-piperidinone (2%), indole (2%), 3-methyl indole (0.6%), pentadecene (1.7%), heptadecane (0.5%).

Example 10

Disodium Hydrogen Phosphate, Method 2

A slurry of 6% microalgae in water and disodium hydrogen phosphate (1.26 g in 300 mL) (7% by weight) was subjected to the procedures of Method 2. A GCMS analysis of a methylene chloride extract of the oil gave (as per centages of that extract that volatalized properly:

In the supercritical reactions, oil phase (33% yield): toluene (5.0%), ethyl benzene (10.2%), 2,5-dimethyl pyrazine (1.3%), trimethyl pyrazine (2.8%), 2-methylcyclopent-2-en-1-one (1.4%), 2,3-dimethylcyclopent-2-en-1-one (2.1%), p-cresol (3.0%), N-ethyl 2-pyrrolidinone (3.5%), 2-piperidinone (3.1%), indole (3.0%), 3-methyl indole (1.4%), pentadecene (3.4%), pentadecane (3.3%), heptadecane (1.5%), hexadecanamide (0.5%) and numerous unidentified products.

Aqueous phase extracts (6.3% yield): acetic acid (25.9%), mixture N-acetylethylene diamine and acetamide (7.5%), hexanoic acid (8.0%), 2-propylmalonic acid (3.6%), butanamide (3.4%), N-methyl 2-pyrrolidinone (3.2%), N-ethyl-2-pyrrolidinone (3.7%) and numerous unidentified products.

In the subcritical range, oil phase (53% yield): toluene (3%), ethyl benzene (6.3%), styrene (2.5%), methyl pyrazine (2.9%), 2,5-dimethyl pyrazine (2.7%), trimethyl pyrazine (2.8%), cyclopentanone (1%), 2-methylcyclopent-2-en-1-one (1.3%), 2,3-dimethylcyclopent-2-en-1-one (1.3%), p-cresol (1.2%), p-ethyl phenol (2.1%), N-ethyl 2-pyrrolidinone (1.7%), 2-piperidinone (5.4%), indole (1.4%), pentadecene (3.4%), pentadecane (2.5%), heptadecane (1.8%), tetramethyl 2-hexadecene (3.4%) and numerous unidentified products.

Aqueous phase extracts (10% yield): acetic acid (28.4%), acetamide (9%), butanoic acid (3.7%), butanamide (4.5%), 2-pyrrolidinone (6.8%), 2-piperidione (9.3%), 6-methyl-3-pyridinol (9.8%) and numerous unidentified products.

Example 11

Sodium Dihydrogen Phosphate, Method 2

A slurry of 6% microalgae in water and sodium dihydrogen phosphate (1.25 g in 300 mL) (7% by weight) was subjected to the procedures of Method 2. A GCMS analysis of a methylene chloride extract of the oil gave (as per centages of that extract that volatalized properly):

Supercritical oil phase (32.5% yield): toluene (6.2%), ethyl benzene (9.5%), xylene (1.9%), styrene (1.1%), methyl pyrazine (1.2%), 2,5-dimethyl pyrazine (1.4%), trimethyl pyrazine (2.3%), 2-methylcyclopent-2-en-1-one (1.8%), 2,3-dimethylcyclopent-2-en-1-one (2.1%), p-cresol (1.5%), p-ethyl phenol (2%), N-ethyl 2-pyrrolidinone (3.3%), pentadecene (1.7%), pentadecane (2.0%), hexadecanamide (1.6%) and numerous unidentified products.

Supercritical aqueous phase extracts (5.2% yield): propanoic acid (4.5%), butanoic acid (12.8%), (2-ethyl butyric+ hexanoic acid (6.1%) valeric acid (4.3%) N-methyl 2-pyrrolidinone (4.6%), 2-pyrrolidinone (3.4%), 2-piperidinone (8.4%), benzenepropanoic acid (6.8%) and numerous unidentified products.

Subcritical oil phase (% yield): toluene (2.8%), ethyl benzene (4.6%), styrene (2.3%), 2,5-dimethyl pyrazine (1.9%), trimethyl pyrazine (5%), 2,3-dimethylcyclopent-2-en-1-one (1.6%), p-cresol (1.5%), N-ethyl 2-pyrrolidinone (1%), %), N-butyl 2-pyrrolidinone (1.3%), 2-piperidinone (5.1%), indole (1.8%), 3-methyl indole (2.3%), pentadecene (1.7%), pentadecane (2.1%), heptadecane (1.5%), hexadecanamide (1.5%) tetramethyl hexadec-2-ene (3.3%), oleiamide (1.3%) and numerous unidentified products.

Subcritical aqueous phase extracts (5.2% yield): acetic acid (21.5%), propanoic acid (4.9%), butanoic acid (7.9%), N-methyl 2-piperidine (4.1%), and numerous unidentified products.

Example 12

Ammonium Dihydrogen Phosphate, Method 2

A slurry of 6% microalgae in water and ammonium dihydrogen phosphate (0.13M) (5% by weight) was subjected to the procedures of Method 2. A GCMS analysis of a methylene chloride extracts of the supercritical reactions gave (as per centages of that extract that volatalized properly):

Oil phase (20% yield): toluene (2.6%), ethyl benzene/xylene (6.0%), probably pyridine and picolinic acid (~10%), trimethyl pyrazine (2.1%), 2,3-dimethylcyclopent-2-en-1-one (1.6%), tetramethylpyrrole (0.9%), pentadecene (1.5%), heptadecane (2.3%), 2-heptadecanone (0.9%), 3-eicosyne (2.0%).

Aqueous phase extracts (6% yield): acetic acid (9.7%), acetamide (10.5%), propanamide (4.2%), butanamide (3.4%), N-methyl 2-pyrrolidinone (3.1%), 2-pyrrolidinone (5.9%), 2-piperidinone (8.2%), benzenepropanoic acid (7.8%), 4-(2-hydroxyethyl)phenol (5.2%) and numerous unidentified products.

Example 13

Ammonium Dihydrogen Phosphate Plus Phosphoric Acid, Method 2

A slurry of 6% microalgae in water and ammonium dihydrogen phosphate (0.13M) (5% by weight) together with sufficient phosphoric acid to bring the pH to 5.5 was subjected to the procedures of Method 2. A GCMS analysis of a methylene chloride extract of the oil in the supercritical reactions gave (as per centages of that extract that volatalized properly):

Oil phase (29% yield): toluene (5.4%), ethyl benzene (8.4%), trimethyl pyrazine (1.3%), cyclopentanone (1.23%), 3-methylcyclopent-2-en-1-one (1.5%), 2,3-dimethylcyclopent-2-en-1-one plus N-methyl-2-pyrrolidinone (7.5%), 2,3,4-trimethylcyclopent-2-en-1-one (5.1%), tetramethyl pyrrole (1%), 3-methyl indole (0.9%), N-ethyl-2-pyrrolidinone (2.4%), 4-ethyl phenol (1.9%), pentadecene (1%), heptadecane (0.9%), hexadecanoic acid (2.8%), hexadecanamide (2.2%), oleiaminde (1.2%).

Aqueous phase extracts (7% yield): Aqueous phase: acetic acid (16.2%), propionic acid (3.7%), isobutyric acid (2.6%), acetamide (6.4%), butanoic acid (12%), hexanoic acid (3.8%), 2-methyl butanoic acid (3.3%), valeric acid (2%), butanamide (3.1%), N-methyl 2-pyrrolidinone (1.7%), 2-pyrrolidinone (4%), 2-piperidinone (5%). and numerous unidentified products.

Example 14

Concentrated Ammonium Hydrogen Phosphate, Method 3

A slurry of 9% microalgae in water and ammonium dihydrogen phosphate (1.3M) adjusted to pH 8 was subjected to the procedures of Method 3, which is effectively the same as method 1, except that it was at pilot scale. A GCMS analysis of a methylene chloride extracts of a sample of the supercritical reaction product gave (as per centages of that extract that volatalized properly):

Oil phase: toluene (5.4%), ethyl benzene (3.4%), styrene (1.8%), 1,3-diazine (5.5%), pyridine (5%), N-ethyl pyrrole (0.6%), methyl pyrazine (14.5%), 2,5-dimethyl pyrazine (7.9%), ethyl pyrazine (4.3%), trimethyl pyrazine (5.8%), 4,6-dimethylpyrimidine (4.6%), cyclopentanone (1.2%), 2-methylcyclopent-2-en-1-one (1.2%), 2,3-dimethylcyclopent-2-en-1-one (1.3%), indole (0.3%), 3-methyl indole (0.7%), hydantoin, (2%), N-methyl succinimide (1.9%), 4-ethyl phenol (0.9%), pentadecene (1.6%), heptadecane (0.9%), hexadecanamide (0.6%), 3.2% miscellaneous condensed pyrazines, and numerous unidentified products.

Example 15

Ammonium Phosphate pH 8.5, Method 2

A slurry of 6% microalgae in water and ammonium hydrogen phosphate (0.13M) (5% by weight) adjusted to pH 8.5 with ammonia was subjected to the procedures of Method 2. A GCMS analysis of a methylene chloride extracts of a sample of the supercritical reaction product gave (as per centages of that extract that volatalized properly):

Supercritical reaction, oil phase (31.5% yield): dimethyl trisulphide (1.9%), toluene (12.7%), ethyl benzene (12.6%), xylene (3%), 5-methyl-5-hexen-2-ol (2.6%), isopentyl alcohoil (7.3%), cyclopentanone (2.8%) 2-methylcyclopentanone (2.4%), 2,3-dimethylcyclopent-2-en-1-one (3.2%), pyridine (0.3%), hydantoin (2.2%), dodecane (0.8%), pentadecene (1.4%), pentadecane (1.6%), heptadecane (0.8%), and numerous unidentified products.

Supercritical reaction, aqueous phase (12.6% yield): acetic acid (20.6%), propanoic acid (5.7%), isobutyric acid (4.4%), butanoic acid (17.8%), 2-methyl butanoic acid (3.9%), hexanoic acid (0.9%), 4-methyl pentanoic acid (5%), acetamide (3.3%), 2-piperidinone (6.1%), and numerous unidentified products.

Example 16

Calcium Phosphate, Method 1

To a 4% suspension of microalgae in water, 15 mL/L of 0.25M phosphoric acid (1% by weight) was added, followed by calcium hydroxide until a pH of 9 was reached. The resultant suspension with the insoluble calcium phosphate was treated according to Method 1. A GCMS analysis of a methylene chloride extract of the oil from the reactions gave (as per centages of that extract that volatalized properly):

Supercritical reaction, oil phase: toluene (2.3%), ethyl benzene (3.2%), N-methylpyrrole (3%), pyrrole (3%), methyl pyrazine (2.8%), 2,5-dimethyl pyrazine (0.9%), methylcyclopent-2-en-1-one (1.3%), butyrolactone (0.7%), p-ethyl phenol (1%), N-methyl succinimide (2.6%), 1-ethyl-2-pyrrolidinone (1%), 2-piperidinone (3.5%), indole (3.2%), 3-methyl indole (1.4%), pentadecene (3.6%), pentadecane (2.8%), heptadecane (2.5%), hexadecanoic acid (5%), hexadecanamide (2.2%) and numerous unidentified products.

Subcritical reaction, oil phase: pyrimidine (1.7%), pyrrole (1.5%), methyl pyrazine (3.5%), 2,5-dimethyl pyrazine (2.3%), ethyl pyrazine (1.3%) 2-methylcyclopent-2-en-1-one (1.5%), 2-pyrrolidinone (0.4%), N-methylsuccinimide (1%), 2-piperidinone (3.35%), indole (2.1%), pentadecene (2.1%), pentadecane (2.7%), heptadecene (1.5%) heptadecane (1.8%), hexadecanoic acid (11.6%), hexadecanamide (6.1%) oleiamide (2.4%), unidentified, but possibly oleic acid (15.3%) and numerous unidentified products.

Example 17

Magnesium Ammonium Phosphate, Method 1

A slurry of 4% microalgae in water and magnesium ammonium phosphate (20 g/L) (2% by weight) was subjected to the procedures of Method 1. A GCMS analysis of a methylene chloride extract of the oil in the supercritical reactions gave (as per centages of that extract that volatalized properly):

Supercritical reaction, oil phase: toluene (2.2%), pyrimidine (6.6%), methyl pyrazine (9.4%), 2,5-dimethyl pyrazine (2.8%), ethyl pyrazine (4.1%), 2-methyl cyclopen-2-en-1-one (3%), 3-methyl cyclopen-2-en-1-one (2.6%), butyrolactone (1.6%), 5-methyl 2-furaldehyde (1.1%), phenol, (1.3%), p-cresol (3.9%), 2-pyrrolidinone (2.3%), N-methyl succinimide (2.2%), 2-piperidinone (6.2%), indole (2.8%), 3-methyl indole (0.8%), pentadecene (1.4%), and numerous unidentified products.

Subcritical reaction, oil phase: pyrimidine (1.9%), methyl pyrazine (5.6%), 2,5-dimethyl pyrazine (3.5%), ethyl pyrazine (2.5%), 2-methyl cyclopen-2-en-1-one (2.7%), 3-methyl cyclopen-2-en-1-one (0.7%), 2-pyrrolidinone (0.9%), N-methyl succinimide (2.2%), 2-piperidinone (4.7%), indole (2.1%), pentadecene (2.8%), dodecanoic acid (1.5%), and numerous unidentified products.

Example 18

Ferric Phosphate, Method 2

A slurry of 6% microalgae in water and ferric phosphate (1.26 g in 300 mL) (7% by weight) was subjected to the procedures of Method 2. A GCMS analysis of the methylene chloride extracts gave (as per centages of that extract that volatalized properly):

Supercritical reaction, oil phase: toluene (2.9%), ethyl benzene (3.4%), trimethyl pyrazine (2.7%), 2-methylcyclopent-2-en-1-one (1.3%), 2,3-dimethylcyclopent-2-en-1-one (1.7%), N-methyl 2-pyrrolidinone (5.4%), N-ethyl 2-pyrrolidinone (2.9%), tridecene (0.8%), pentadecene (1.2%), pentadecane (1.6%), heptadecane (0.8%) and numerous unidentified products.

Subcritical reaction, (½ hr at 350° C.), oil phase: dimethyl disulphide (8.3%), toluene (5.5%), ethyl benzene (7.9%), xylene (1.5%), styrene (2.1%), 2-methylcyclopent-2-en-1-one (1.4%), 2,3-dimethylcyclopent-2-en-1-one (1%), methyl pyrazine (2.4%), 2,5-dimethyl pyrazine (2.1%), trimethyl pyrazine (2.1%), p-ethyl phenol, 2%), pentadecene (2.2%), and numerous unidentified products.

Supercritical reaction, aqueous phase: possibly acetic acid (9.9%). propanoic acid (7.2%), isobutyric acid (5.7%), butanoic acid (29.4%), isovaleric acid (5.4%), 2-methyl butyric (8.4%) valeric acid (1.9%), butanamide (5.9%)) and numerous unidentified products.

Subcritical reaction, (½ hr at 350° C.), aqueous phase: acetic acid (24.2%), propanoic acid (7.1%), isobutyric acid (5.7%), butanoic acid (14.9%), hexanoic acid (1%), 4-methyl pentanoic acid (4.5%), acetamide (3.7%), 2-piperidinone (4%), and numerous unidentified products.

Example 19

Aluminium Phosphate, Method 2

A slurry of 6% microalgae in water and aluminium phosphate (1.26 g in 300 mL) (7% by weight) was subjected to the procedures of Method 2. A GCMS analysis of the methylene chloride extracts gave (as per centages of that extract that volatalized properly):

Supercritical reaction, oil phase: Probably mixture of pyridine and pyrimidine (16.9%), toluene (2.2%), xylene (10%), styrene (1.1%), 2-methylcyclopent-2-en-1-one (1.4%), 2,3-dimethylcyclopent-2-en-1-one (1.8%), 2,5-dimethyl pyrazine (1.7%), trimethyl pyrazine (3.4%), N-methyl 2-pyrrolidinone (4.2%), N-ethyl 2-pyrrolidinone (2.6%), tridecene (0.8%), pentadecene (1.4%), pentadecane (1.3%), heptadecane (0.6%) and numerous unidentified products.

Subcritical reaction, (1 hr at 350° C.), oil phase: 2,3-dimethylcyclopent-2-en-1-one (1.3%), trimethyl pyrazine (1.8%), N-ethyl 2-pyrrolidinone (1.7%), N-butyl 2-pyrrolidinone (3.4%), 2-piperidinone (6.7%), indole (1.6%), phenol (2.8%), pentadecene (3.4%), probably pentadecane (2.9%), heptadecane (2.3%), tetramethyl hexadecene (4.3%), hexadecanamide (1.2%) and numerous unidentified products.

Subcritical reaction, (½ hr at 350° C.), oil phase: dimethyl disulphide (4.1%), toluene (6.2%), ethyl benzene (9.7%), styrene (2%), 5-methyl-5-hexen-2-ol (0.9%), 2-methylcyclopent-2-en-1-one (1.3%), 2,3-dimethylcyclopent-2-en-1-one (2%), 2,5-dimethyl pyrazine (2.4%), trimethyl pyrazine (3.9%), N-ethyl 2-pyrrolidinone (2%), tridecene (1.1%), pentadecene (3.3%), pentadecane (2.5%), heptadecane (1.5%), hexadecanamide (0.9%) and numerous unidentified products.

Supercritical reaction, aqueous phase: propanoic acid (5.2%), acetamide (9.4%), butanoic acid (17.3%), butanamide (4.4%), N-methyl succinimide (7.4%), N-ethyl-2-pyrrolidinone (0.4%), 2-piperidinone (13.7%), benzenepropanoic acid (8.3%), and numerous unidentified products.

Subcritical reaction, (1 hr at 350° C.), aqueous phase: butanamide (3.1%), N-methyl-2-pyrrolidinone (1.4%), 2-pyrrolidinone (3.4%), 2-piperidinone (<7.1%), benzenepropanoic acid (4.6%), oleic acid (0.9%), oleiamide (1.1%) and numerous unidentified products.

Subcritical reaction, (½ hr at 350° C.), aqueous phase: acetic acid (18.7%), acetamide (5.5%), N-acetylethylenediamine (3.5%), piperidine (2.9%), butanoic acid (6.8%), butanamide (3.2%), 2-pyrrolidinone (4.8%), 2-piperidinone (<10%), benzenepropanoic acid (8.3%), oleic acid (0.9%), oleiamide (1.1%) and numerous unidentified products.

Example 20

Cellulose, Ammonium Phosphate, Method 1

A slurry of 1% microfine cellulose in water and ammonium hydrogen phosphate (1.32 g in 1 L) (13% by weight) was subjected to the procedures of Method 1. There was usually a residual black solid that we interpreted as carbon, and we also found that the products were generally soluble in water, and had to be extracted. A GCMS analysis of a methylene chloride extract gave (as per centages of that extract that volatalized properly):

in the subcritical solution: methyl pyrazine (0.8%), 2,5-hexanedione (1.6%), butyrolactone (0.9%), 5-methyl-2-furaldehyde (1.6%), cyclopentanone (5.8%), cyclopent-2-en-1-one (17.3%), 2-methylcyclopent-2-en-1-one (15.2%), 3-methylcyclopent-2-en-1-one (6.5%), 2,3-dimethylcyclopent-2-en-1-one (3%), 3-methyl-1,2-cyclopentanedione (3.4%) and numerous unidentified products.

in the supercritical solution: 2,5-hexanedione (0.9%), cyclopentanone (6%), cyclopent-2-en-1-one (14.3%), 2-methylcyclopent-2-en-1-one (16.5%), 3-methylcyclopent-2-en-1-one (7.8%), 2,3-dimethylcyclopent-2-en-1-one (3.4%), 3-methyl-1,2-cyclopentanedione (2.9%) and numerous unidentified products.

Example 21

Blue-Green Algae, Method 2

A slurry of 8% cyanobacteria (predominantly Aphanizomenon) in water and trisodium phosphate (1.2 g in 300 mL) (5% by weight) was subjected to the procedures of Method 2 under supercritical conditions. A GCMS analysis of a methylene chloride extract of the oil gave (as per centages of that extract that volatalized properly):

toluene (2.8%), ethyl benzene (12.6%), styrene (2.2%), methyl pyrazine (1.8%), 2,5-dimethyl pyrazine (2%), trimethyl pyrazine (2%) 2,3-dimethylcyclopent-2-en-1-one (5.3%), p-cresol (3.3%), p-ethyl phenol (4%), N-ethyl-2-pyrrolidinone (3.5%), N-butyl-2-pyrrolidinone (5.5%), indole (0.8%), 3-methyl indole (1.3%), tridecene (0.8), pentadecene (1.9%), heptadecane (4.3%), hexadecanamide (1%), and numerous unidentified products.

Example 22

Cellulose, Sodium Phosphate, Method 1

Example 20 was repeated, except that trisodium phosphate replaced ammonium hydrogen phosphate (0.5 g/1 L) (5% by weight). A GCMS analysis of a methylene chloride extract gave (as per centages of that extract that volatalized properly):

in the subcritical solution: toluene (1.5%), 2,5-hexanedione (0.5%), cyclopentanone (1.9%), cyclopent-2-en-1-one (10.7%), 2-methylcyclopent-2-en-1-one (6.3%), 3-methylcyclopent-2-en-1-one (3.4%), 2,3-dimethylcyclopent-2-en-1-one (0.8%), 3-methyl-1,2-cyclopentanedione (3.4%) and numerous unidentified products.

in the supercritical solution: toluene (1.7%), 2,5-hexanedione (0.7%), butyrolactone (1.3%), cyclopentanone (5.2%), cyclopent-2-en-1-one (13.9%), 2-methylcyclopent-2-en-1-one (15.9%), 3-methylcyclopent-2-en-1-one (4.9%), 2,3-dimethylcyclopent-2-en-1-one (3.4%), 3-methyl-1,2-cyclopentanedione (4.8%), dodecane (0.7%) and numerous unidentified products.

Example 23

Kelp, Sodium Phosphate, Method 2

A slurry of 10% previously dry ground Macrocystis in water and trisodium phosphate (0.5 g in L) (5% by weight) was subjected to the procedures of Method 2 under supercritical conditions. A GCMS analysis of a methylene chloride extract of the oil gave (as per centages of that extract that volatalized properly):

Oil phase: toluene (2.7%), xylene (2.6%), N-ethyl pyrrole (1.7%), cyclopentanone (3.8%), 2-methyl cyclopentanone (3.2%), 2-methylcyclopent-2-en-1-one (5.9%), 3-methylcyclopent-2-en-1-one (3.3%), unidentified isomer of 2,3-dimethylcyclopent-2-en-1-one (3.1%), 2,3-dimethylcyclopent-2-en-1-one (7.4%), 2,3,4-trimethylcyclopent-2-en-1-one (3.2%), 3,4-dimethylcyclopent-2-en-1-one (3.2%), p-cresol (1.5%), p-ethyl phenol (2.8%), tridecene (0.4%), 3-methyl indole (0.7%), pentadecene (0.9%), heptadecane (0.6%) and numerous unidentified products.

Aqueous phase: acetic acid (12%), N-ethyl-2-pyrrolidinone (0.1%) dianhydromannitol (22.6%), 1,4:3,6-dianhydroglucitol (11.9%) and numerous unidentified products.

INDUSTRIAL APPLICATION

The method of the invention may be used to produce:
(a) materials such as aromatic hydrocarbons, linear alkanes and alkkenes, and lightly oxygenated volatile hydrocarbons able to be used directly as additives to fuel, (b) material which may be refined by processes such as hydrotreating and cracking as known to those practised in the art to make fuels,
(c) chemical products which may act as feedstock for other chemicals,
(d) pyrazines that may be used directly as flavour enhancers,
(e) polymethylated pyrazines that may be oxidized to make diacids suitable for biopolymers, particularly hydrophilic biopolymers.
(f) diols that may be used to make hydrophilic biopolymers such as polyesters,
(e) ethyl benzene, which would be a bioprecursor to styrene, or styrene itself, which permits a renewable source of polystyrene, and related polymers such as an unsaturated polyester component, an ABS component, etc.

The foregoing description of the invention includes preferred forms thereof. Modifications may be made thereto without departing from the scope of the invention.

What we claim is:

1. A method for producing one or more organic chemical products from biomass comprising:
   (i) heating an aqueous slurry comprising biomass and water in a pressure vessel at a temperature of about 150° C. to about 500° C. in the presence of a phosphate catalyst to produce a mixture comprising a dispersion of an organic phase and an aqueous phase, and
   (ii) separating one or more organic chemical products from the mixture.

2. The method of claim 1, wherein the aqueous slurry comprises about 1 to about 80% by weight biomass.

3. The method of claim 1, wherein the aqueous slurry comprises about 1 to about 20% by weight phosphate catalyst.

4. The method of claim 1, wherein the aqueous slurry is heated at a temperature of about 300° C. to about 374° C.

5. The method of claim 1, wherein the aqueous slurry is heated at a temperature of about 374° C. to about 500° C.

6. The method of claim 1, wherein the aqueous slurry is heated for about 1 to about 240 minutes.

7. The method claim 6, wherein the aqueous slurry is heated for about 5 minutes to about 60 minutes.

8. The method of claim 1, wherein the biomass is selected from algal biomass, cellulosic biomass, proteinaceous biomass and seaweed, or any combination of any two or more thereof.

9. The method of claim 1, wherein the phosphate catalyst comprises a phosphate anion and one or more monovalent counterions, or one or more divalent counterions, or one or more trivalent counterions, or any combination of any two or more thereof.

10. The method of claim 9, wherein the one or more counterions are selected from the group comprising hydrogen, lithium sodium, potassium, rubidium, caesium, ammonium, magnesium, calcium, barium, strontium, zinc, cadmium, copper, nickel, cobalt, manganese, vanadyl, tin, leads, ferrous, ferric, aluminium, chromic, scandium and rare earths ions, or any two or more thereof.

11. The method of claim 1, wherein the pH of the aqueous slurry is adjusted to a pH of about 7 to about 11.

12. The method of claim 1, wherein the pH of the aqueous slurry is adjusted to a pH of about 7 to about 11 by the addition of ammonia.

13. The method of claim 1, wherein the one or more organic chemical products are selected from pyrazines, hydrocarbons, alkenes, alkanes, methylated pyrroles, imides, amides, lactams, crotonaldehyde, saturated and unsaturated aldehydes and ketones, carboxylic acids, lipid acids, phenols, and cresol.

14. The method of claim 1, wherein the biomass comprises a seaweed in the phaeophyta or any alginate bearing material and the one or more organic chemical products are dianhydromannitol and/or dianhydroglucitol.

15. The method of claim 1, wherein the biomass is microalgae and the method comprises:
    (i) heating an aqueous slurry of microalgae in a pressure vessel at a temperature of about 330° C. to about 450° C. to produce an organic phase and an aqueous phase, and
    (ii) separating pyrazines and lactams from the mixture.

16. The method of claim 1, wherein the amount of water present is sufficient to maintain an aqueous phase if subcritical or to maintain the pressure for water if supercritical at the selected temperature.

17. The method of claim 13, wherein
    (i) the one or more pyrazines is methyl, dimethyl, trtimethyl, ethyl, or ethylmethyl pyrazine;
    (ii) the one or more hydrocarbons is toluene, ethyl benzene, styrene or xylene;
    (iii) the one or more alkenes is 1-nonene or pentadecene;
    (iv) the one or more alkanes is pentadecane, heptadecane or peptadecane;
    (v) the one or more imides is N-methyl succinimide or N-ethyl succinimide;
    (vi) the one or more amides is acetamide, propanamide, butanamide, hexadecanamide or 9-octadecanamide;
    (vii) the one or more lactams is 2-pyrrolidinone, N-methyl-2-pyrrolidinone, N-ethyl-2-pyrrolidinone, N-butyl-2-pyrrolidinone, 2-piperidinone or caprolactam;
    (viii) the one or more saturated or unsaturated aldehydes or ketones is cyclopentanone, cyclopentenone, methyl cyclopentenone, dimethyl cyclopenetenone, methyl furfural or hydroxymethyl furfural;
    (ix) the one or more carboxylic acids is acetic, butanoic, propionic, octanoic, dodecanoic, hexadecanoic, benzene propanoic, methylated butyric or valeric acids; and
    (x) the one or more lipid acids is palmitic or oleic acids.

* * * * *